(12) United States Patent
Netherton

(10) Patent No.: US 12,708,326 B2
(45) Date of Patent: Aug. 18, 2026

(54) NEURODIAGNOSTIC NEEDLE ELECTRODE PAIR ASSEMBLY AND METHOD OF MANUFACTURE

(71) Applicant: ROCWorks, LLC, Prosperity, SC (US)

(72) Inventor: Brett Netherton, Prosperity, SC (US)

(73) Assignee: ROCWorks, LLC, Prosperity, SC (US)

( * ) Notice: Subject to any disclaimer, the term of this patent is extended or adjusted under 35 U.S.C. 154(b) by 255 days.

(21) Appl. No.: 18/738,804

(22) Filed: Jun. 10, 2024

(65) Prior Publication Data

US 2024/0407728 A1 Dec. 12, 2024

Related U.S. Application Data

(60) Provisional application No. 63/472,097, filed on Jun. 9, 2023.

(51) Int. Cl.
*A61B 5/00* (2006.01)
*A61B 5/294* (2021.01)

(52) U.S. Cl.
CPC ........... *A61B 5/6848* (2013.01); *A61B 5/294* (2021.01); *A61B 2562/0209* (2013.01); *A61B 2562/125* (2013.01)

(58) Field of Classification Search
CPC ....... A61B 5/0492; A61B 5/262; A61B 5/271; A61B 5/273; A61B 5/294; A61B 5/296; A61B 5/6848; A61B 2562/0209; A61B 2562/135; A61B 2562/187; A61B 2562/225–227; A61N 1/0502
See application file for complete search history.

(56) References Cited

U.S. PATENT DOCUMENTS

| | | | | |
|---|---|---|---|---|
| 4,932,936 | A * | 6/1990 | Dykstra | A61M 5/427 604/511 |
| 12,102,376 | B2 * | 10/2024 | Callas | A61B 18/14 |
| 2011/0105876 | A1 * | 5/2011 | Zhang | A61B 5/388 600/393 |
| 2011/0238057 | A1 * | 9/2011 | Moss | A61B 18/1477 606/41 |
| 2021/0145341 | A1 * | 5/2021 | Edwards | A61B 5/262 |

* cited by examiner

*Primary Examiner* — Eun Hwa Kim
(74) *Attorney, Agent, or Firm* — BURR & FORMAN LLP

(57) ABSTRACT

A neurodiagnostic needle electrode pair assembly is provided that includes a pair of needle electrodes connected to a pair of leadwires by respective electrical connections between proximal ends of the needle electrodes and distal ends of the leadwires. The neurodiagnostic needle electrode pair assembly includes a needle spacer which has parallel holes in a spaced apart relationship. The needle electrodes extend into and through the parallel holes that define a spacing between the needle electrodes. The neurodiagnostic needle electrode pair assembly includes a recovered heat shrink tube covering the needle spacer, the respective electrical connections and the distal ends of the leadwires. A method of manufacturing a neurodiagnostic needle electrode pair assembly is also provided.

18 Claims, 44 Drawing Sheets

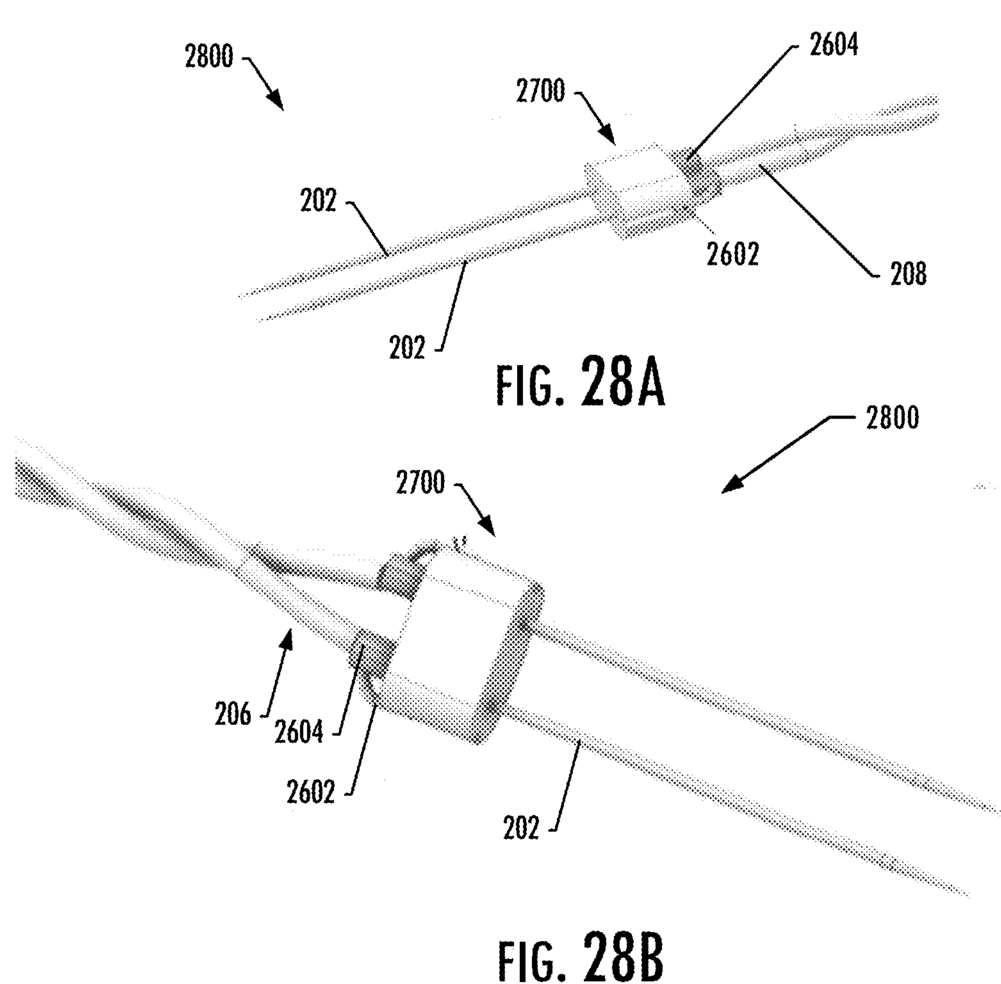
FIG. 28A
FIG. 28B
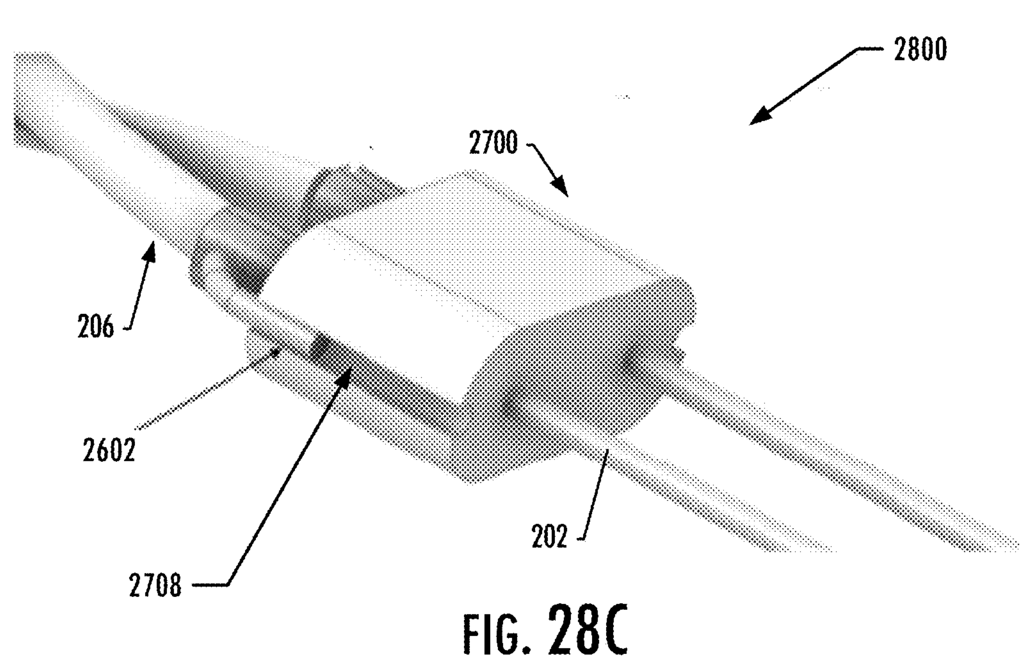
FIG. 28C

NEURODIAGNOSTIC NEEDLE ELECTRODE PAIR ASSEMBLY AND METHOD OF MANUFACTURE

CROSS-REFERENCE TO RELATED APPLICATION(S)

The present application claims priority to U.S. Provisional Patent Application No. 63/472,097, entitled: Neurodiagnostic Needle Electrode Pair and Method of Manufacture, filed on Jun. 9, 2023, the content of which is hereby incorporated by reference.

TECHNOLOGICAL FIELD

The present disclosure relates generally to medical devices, and specifically to a neurodiagnostic needle electrode pair assembly and method of manufacturing the same.

BACKGROUND

The performance of electroneurodiagnostics requires recording physiological bioelectrical signals as well as stimulation of physiologic tissues. This is routinely performed by patient attachment electrodes that are multiple and diverse, often including needle electrodes. Further, needle electrode pairs are not uncommon. Due to the diverse range of physiologic tissue electrical source generators that may be of interest to the clinician, spacing of recording needle electrode pairs and stimulating needle electrode pairs also needs to be diverse, but often includes close spacing.

The techniques used to manufacture paired needle electrodes have included forming the needle electrode pair via injection molding a rigid plastic hub to cover the electrical connections. FIG. 1 illustrates a conventional neurodiagnostic needle electrode pair with an injection molded hub. The electrical connections that are covered by the plastic hub typically include either a solder joint or mechanical crimp to electrically connect the needle with the electrode leadwire. The electrode leadwire then electrically connects the electrode patient attachment with the neurodiagnostic electrical instrumentation equipment. The process of injection molding is well established as an effective way of producing such medical devices. It is also a relatively expensive medical device production technique. Alternative manufacturing techniques that are more cost effective are desired.

BRIEF SUMMARY

An example clinical application benefitting from close recording needle electrode pair spacing includes recordings from the facial nerve, which innervates striated muscles of the face. For instance, the zygomatic branch of the facial nerve typically innervates the orbicularis oculi muscle. The orbicularis oculi is a relatively small striated muscle mass with a high density of motor units. Close placement of small needle electrodes may often be used when recording the relatively small quadrupole electromyographic signal generated from these motor units since this quadrupole physiologic signal attenuates rapidly as a function of the cube of the distance from the physiologic source generator. In this fashion, a clinician has opportunity to record different pools of motor units from each needle in the electrode pair, even though the pair may be closely spaced.

It may be beneficial for the needle electrode pair used to perform the physiologic recording to be ergonomic to the clinician placing the needles. The handhold grip portion of any clinically used needle electrode may typically be referred to as a "hub." Other names may include but are not limited to a "grip," "hold," or other such similar names. For paired needle electrodes that may require a specific inter-needle distance, the hub may facilitate consistency in the needle spacing as well as provide the clinician with a comfortable hub. Also, because the electrical recordings (or likewise stimulation) require electrical exposure only at the needle tip in contact with the patient tissue, the hub of the needle electrode pair may constitute a barrier against fluids that could compromise the electrical integrity of the needle electrode pair by an electrical short circuit inside of the hub.

The present disclosure includes, without limitation, the following example implementations.

Some example implementations provide a neurodiagnostic needle electrode pair assembly comprising: a pair of needle electrodes connected to a pair of leadwires by respective electrical connections between proximal ends of the needle electrodes and distal ends of the leadwires; a needle spacer including parallel holes in a spaced apart relationship, the needle electrodes extending into and through the parallel holes that define a spacing between the needle electrodes; and a recovered heat shrink tube covering the needle spacer, the respective electrical connections and the distal ends of the leadwires.

Some example implementations provide a method of manufacturing a neurodiagnostic needle electrode pair assembly, the method comprising: connecting a pair of needle electrodes to a pair of leadwires by forming respective electrical connections between proximal ends of the needle electrodes and distal ends of the leadwires; extending the needle electrodes into and through parallel holes of a needle spacer, the parallel holes defining a spacing between the needle electrodes; positioning a heat shrink tube over the needle spacer, the respective electrical connections and the distal ends of the leadwires; and applying heat to recover the heat shrink tube covering the needle spacer, the respective electrical connections, and the distal ends of the leadwires.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. The present disclosure is intended to be read holistically such that any separable features or elements of the disclosure, in any of its aspects and example implementations, should be viewed as combinable unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURE(S)

Having thus described example implementations of the disclosure in general terms, reference will now be made to the accompanying figures, which are not necessarily drawn to scale, and wherein:

FIGS. 28A, 28B, 28C and 28D illustrate an extruded needle spacer with side slots in abutment with mechanically crimped needles in the assembly in such a way that the bent needle ends slide into the side slots of the extruded needle spacer, according to some example implementations;

Figure 30A:
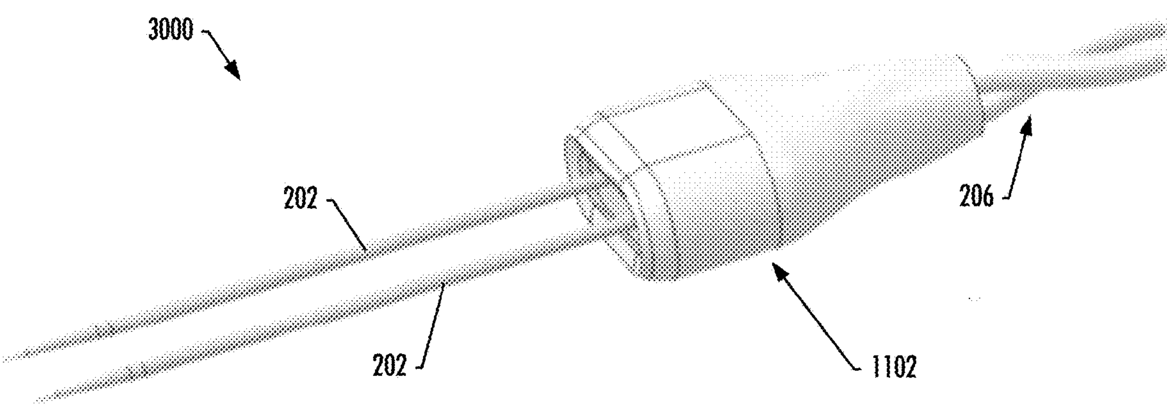
FIGS. 30A and 30B illustrate a neurodiagnostic needle electrode pair utilizing an extruded needle spacer with side slots in abutment with mechanically crimped needles, according to some example implementations.
Figure 30B:
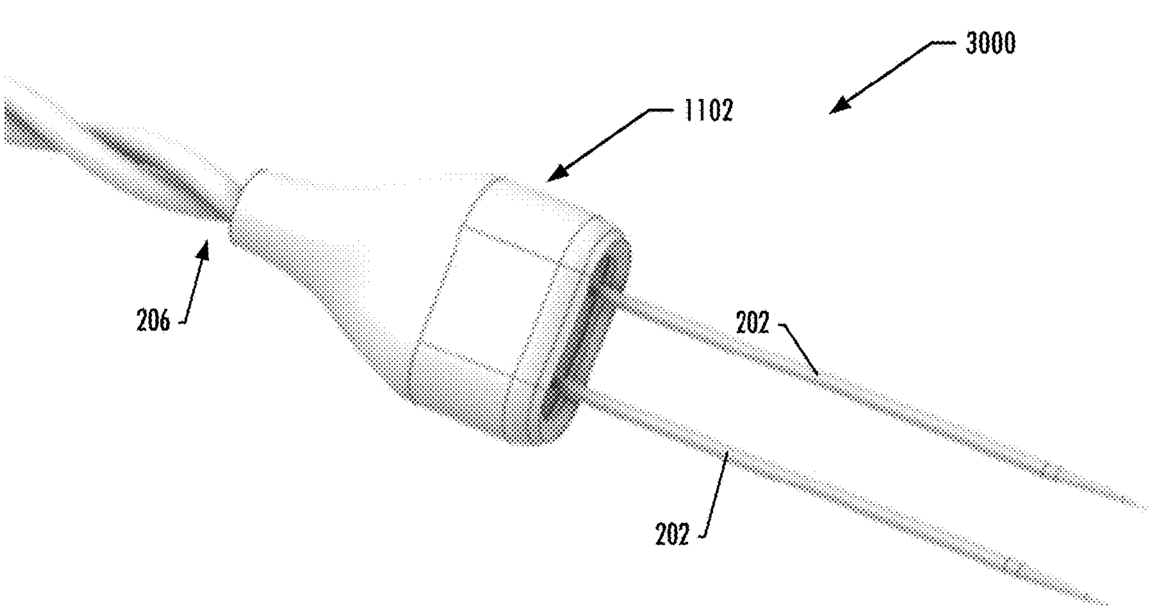
Figure 31:
Figure 31:
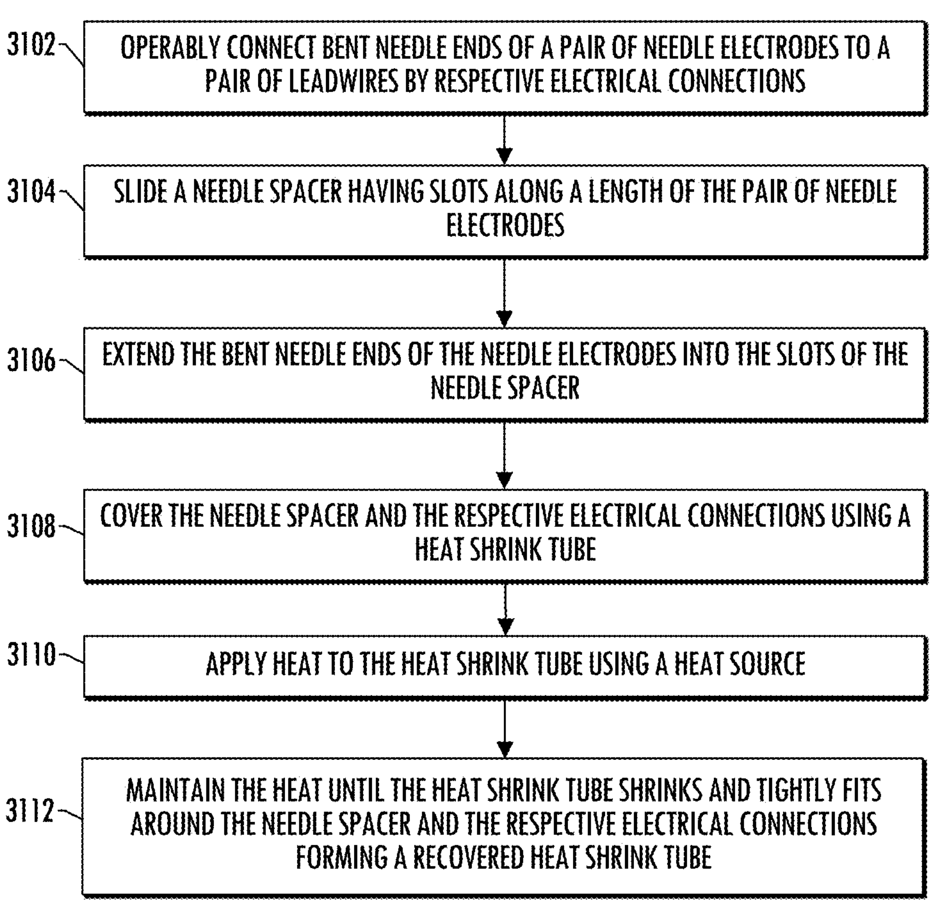

FIG. 31 is a flowchart illustrating various steps in a method of forming a neurodiagnostic needle electrode pair assembly shown in FIGS. 30A and 30B, according to some example implementations; and FIGS. 32A, 32B, 32C, 32D, 32E, 32F and 32G illustrate a process of forming the neurodiagnostic needle electrode pair utilizing an extruded needle spacer with side slots in abutment with mechanically crimped needles shown in FIGS. 30A and 30B, according to some example implementations.

DETAILED DESCRIPTION

Some implementations of the present disclosure will now be described more fully hereinafter with reference to the accompanying figures, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. Like reference numerals refer to like elements throughout.

Unless specified otherwise or clear from context, references to first, second or the like should not be construed to imply a particular order. A feature described as being above another feature (unless specified otherwise or clear from context) may instead be below, and vice versa; and similarly, features described as being to the left of another feature else may instead be to the right, and vice versa. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As used herein, unless specified otherwise or clear from context, the “or” of a set of operands is the “inclusive or”

and thereby true if and only if one or more of the operands is true, as opposed to the "exclusive or" which is false when all of the operands are true. Thus, for example, "[A] or [B]" is true if [A] is true, or if [B] is true, or if both [A] and [B] are true. Further, the articles "a" and "an" mean "one or more," unless specified otherwise or clear from context to be directed to a singular form. Furthermore, it should be understood that unless otherwise specified, the terms "data," "content," "digital content," "information," and similar terms may be at times used interchangeably.

Figure 1:
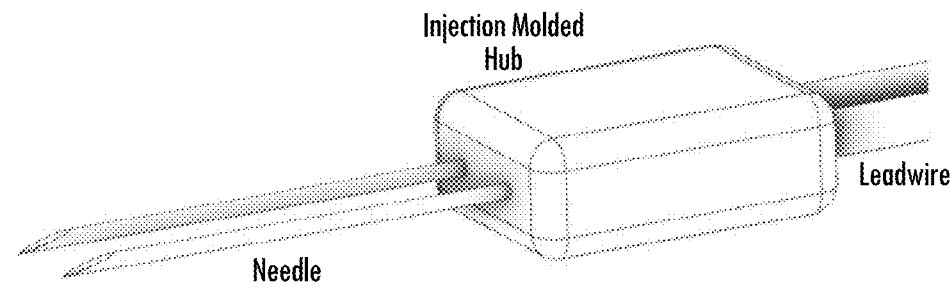
FIG. 1 illustrates a conventional neurodiagnostic needle electrode pair with an injection molded hub.

Example implementations are described herein of manufacturing techniques to produce a paired needle electrode with a hub that does not require the conventional injection molding process yet performs the required functions of the hub and is cost-effective. The example implementations provide an alternative to more expensive injection molding processes that yields a conventional hub as highlighted in FIG. 1, showing a neurodiagnostic needle electrode pair with an injection molded hub.

In some examples, a neurodiagnostic needle electrode pair is manufactured while maintaining at least some of the same structural characteristics/requirements, including: a fluid resistant barrier covering the electrical connections between the needle and the leadwire; and needle separation and inter-needle rigidity. Because of their small wire diameter, the needles may be inherently flexible, however, at their base, they may be manufactured to be well-held in parallel position.

Figure 2A:
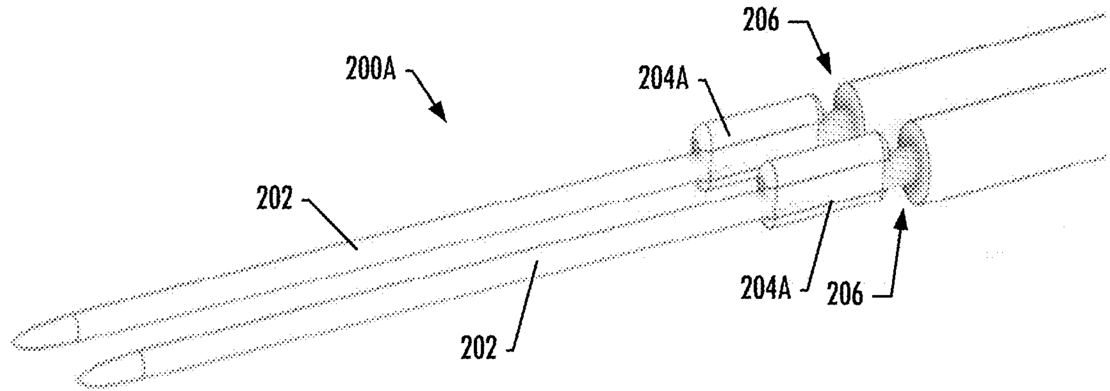
FIGS. 2A, 2B and 2C illustrate neurodiagnostic needle electrode pair subassemblies, according to some example implementations.

More specifically, the example of FIG. 2A illustrates a subassembly 200*a* in which a pair of elongated, metallic needle electrodes is positioned side-by-side. In some examples, each of the needle electrodes includes a sharp point at a distal tip (farther end) for penetration purposes. The subassembly 200A includes a pair of leadwires extending away from proximal ends of the needle electrodes. The pair of leadwires correspond electrical wires responsible for transmitting signals generated by the needle electrodes.

Each needle electrode 202 of the pair of needle electrodes is connected to a corresponding leadwire 206 of the pair of leadwires by an electrical connection that connects the proximal end of the needle electrode 202 to a distal end of the corresponding leadwire 206 of the pair of leadwires. In some examples, the electrical connection include a solder joint 204A at a junction between each needle electrode 202 and its corresponding leadwire 206, as shown in FIG. 2A. The solder joint 204A may create a permanent and electrically conductive joint between the two conductors (the needle electrode 202 and the leadwire 206).

Figure 2B:
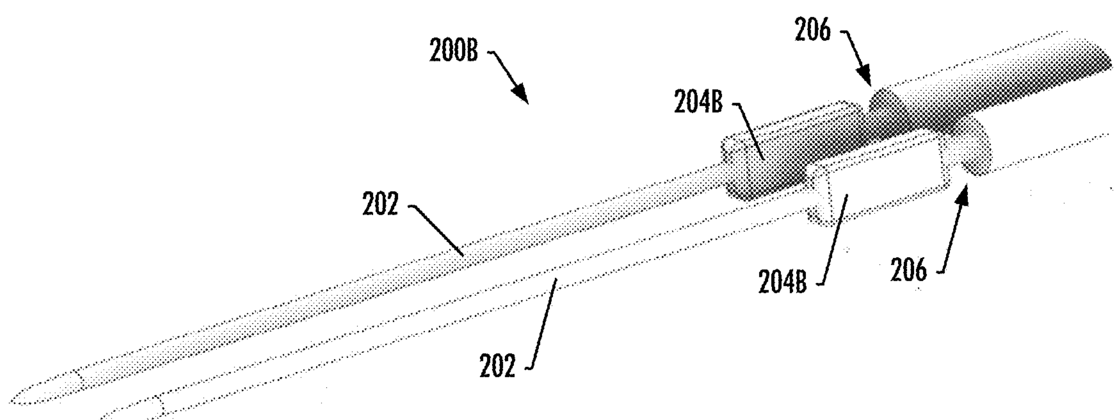

The example of FIG. 2B illustrates a subassembly 200B which may include a mechanical crimp 204B as the electrical connection between the needle electrode 202 and the corresponding leadwire 206. In some examples, the needle electrode 202 and the leadwire 206 may be made from dissimilar materials. Therefore, the mechanical crimp 204B is used in the subassembly 200B which may connect the needle electrode 202 and the leadwire 206. In some examples, the mechanical crimp 204B may have a non-circular cross-section (e.g., an oval, an elliptical, a quadrilateral and the like) that may enhance resistance of the needle electrodes to spin when bent into a bent-needle configuration.

Figure 2C:
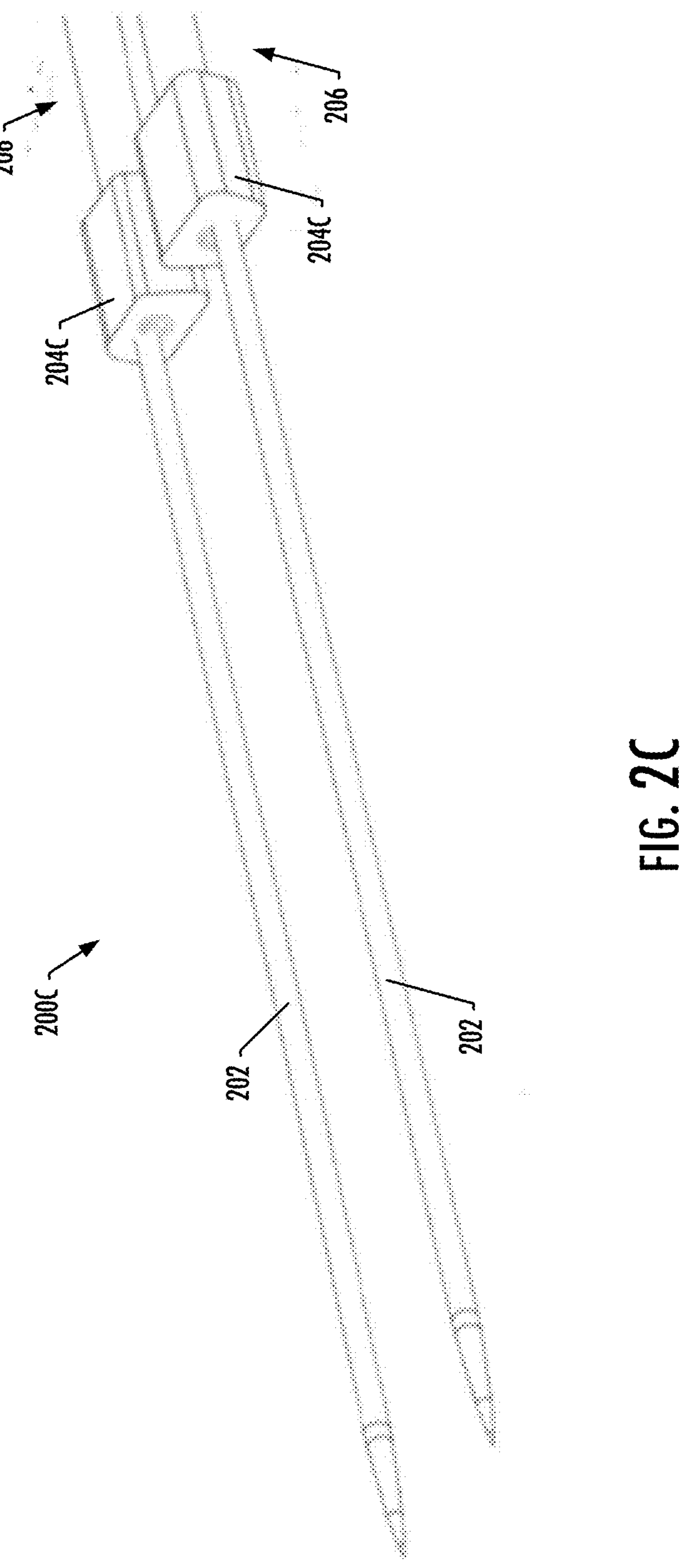

The example of FIG. 2C illustrates a subassembly 200C which may include a mechanical crimp 204C as the electrical connection between the needle electrode 202 and the corresponding leadwire 206. In some examples, the mechanical crimp 204C may be shaped into a conformational shape that can be specifically mated to an identical conformational shaped hole, as shown in FIG. 2C.

Figures 3A, 3B, 3C:
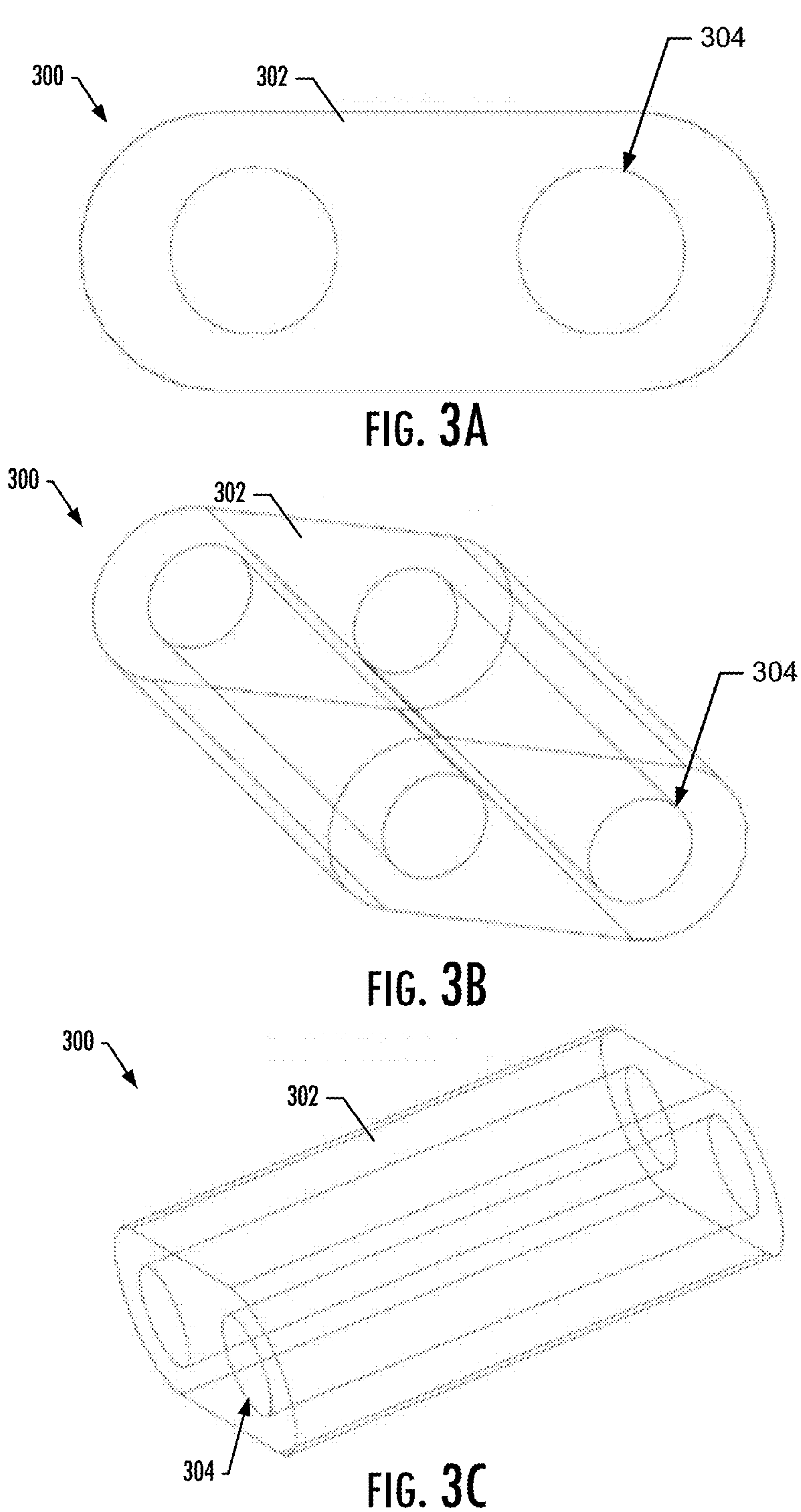
FIGS. 3A, 3B, 3C, 3D and 3E illustrate a leadwire spacer, according to some example implementations.

FIG. 3A shows a front view of a leadwire spacer 300, while FIGS. 3B and 3C show transparent, perspective views of the leadwire spacer 300. The leadwire spacer 300 may be incorporated into the subassemblies 200A, 200B and 200C previously described in FIGS. 2A-2C. The leadwire spacer 300 is designed to accommodate the electrical connections (e.g., solder joint or mechanical crimp) formed between the needle electrode 202 and the corresponding leadwire 206 as shown in FIGS. 2A-2C. The leadwire spacer 300 may enable to organize and protect one or more connection points within the subassemblies. In some examples, the leadwire spacer 300, by partially encasing the pair of leadwires near the electrical connections, can alleviate strain on the electrical connections during manipulation or bending of the neurodiagnostic needle electrode pair assembly. The leadwire spacer 300, when combined with adhesive filling a potential void around the electrical connections, can further secure the electrical connections and add rigidity to the subassemblies 200A, 200B and 200C.

The leadwire spacer 300 includes a body 302. The body 302 of the leadwire spacer 300 is a rigid structural element, typically formed from a high-durometer (yet somewhat flexible) plastic material through an extrusion process. The leadwire spacer 300 incorporates two elongated holes 304 that run parallel to each other and to a longitudinal axis of the body 302. As described herein, these and similar holes may at times be referred to as lumens. The holes 304 are designed to receive the leadwires 206 and accommodate the electrical connections (e.g., solder joint or mechanical crimp) formed between the needle electrode 202 and the leadwire 206. The size of the holes 304 may be configured to allow the leadwire spacer 300 to slide easily onto the leadwires 206 while providing a secure fit.

Figure 3D:
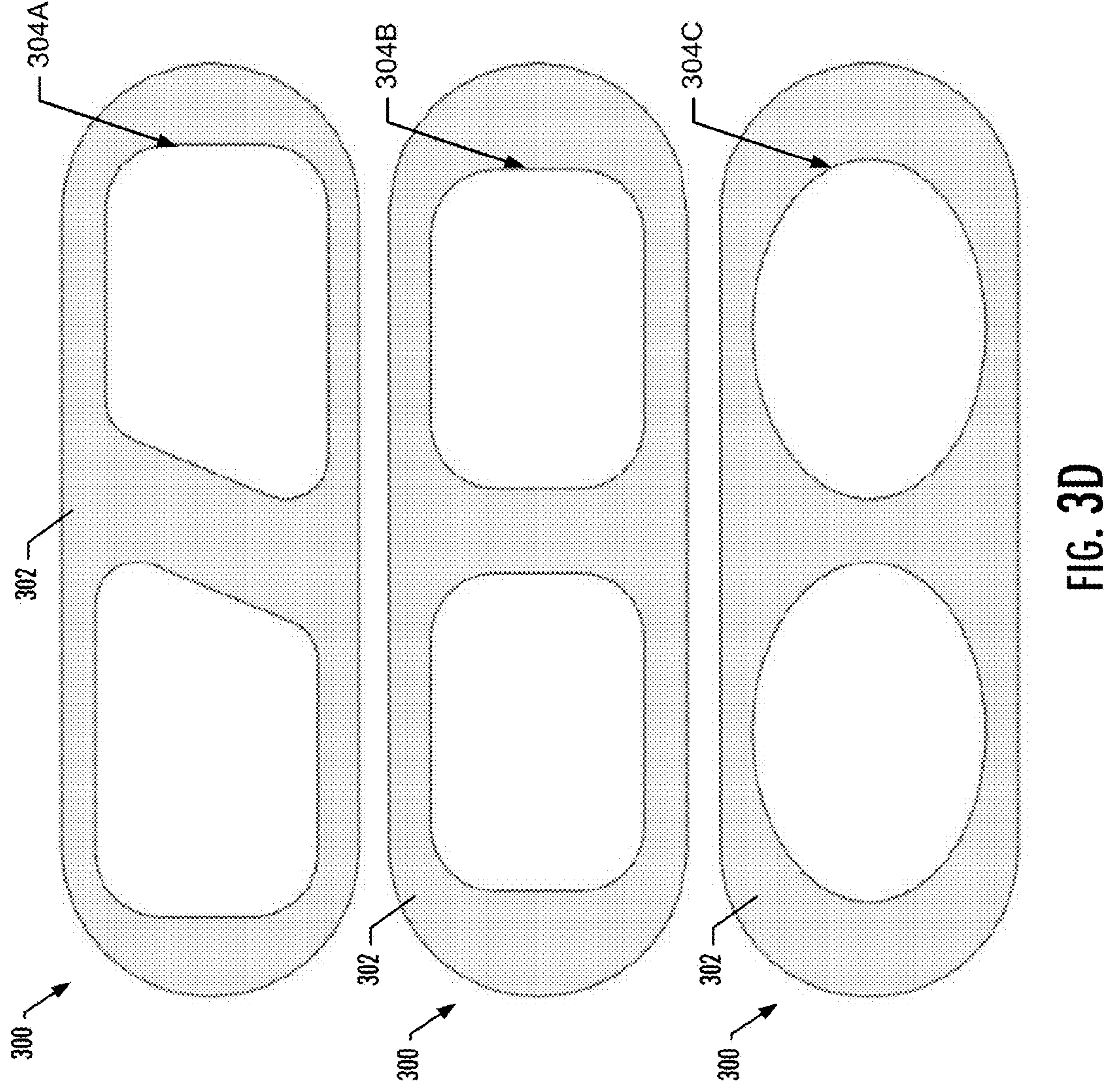
Figure 3E:
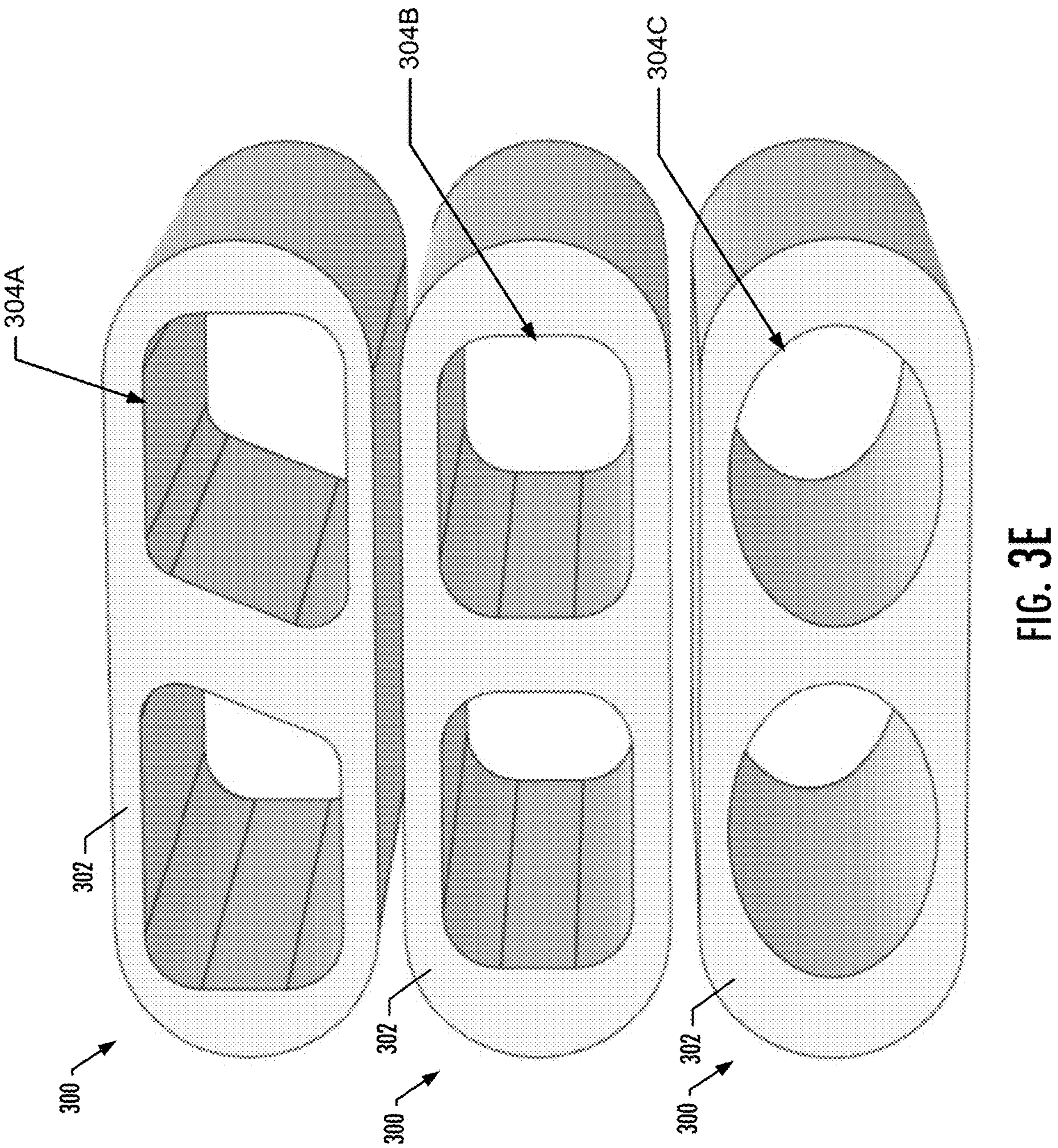

FIGS. 3D and 3E depict variations of the leadwire spacer 300 introduced in FIGS. 3A-3C. These figures specifically focus on the holes 304 within the body 302 and their potential for variable shapes. Unlike FIGS. 3A-3C, which showed a more generic hole shape, FIGS. 3D and 3E showcase a plurality of leadwire spacers each with the holes of various shapes to accept specifically shaped mechanical crimps. In some examples, a hole 304A has a conformational shape. The conformational shape is designed to precisely mate with a correspondingly shaped mechanical crimp, such as the mechanical crimp 204C, as disclosed in FIG. 2C. Interlocking between the mechanical crimp 204C and the hole 304A may distribute stress more evenly, leading to stronger and more stable electrical connections. The mechanical crimp 204C and the hole 304A of the leadwire spacer 300 may be used for applications where the neurodiagnostic needle electrode pair assembly may experience bending or manipulation during use. Alternatively, a hole 304B (e.g., rectangular shaped) and a hole 304C (e.g., oval shaped) may be used with a standard, non-conformational mechanical crimp (e.g. 204B) or the solder joint 204A. These may accommodate a wider range of crimp shapes while still providing a secure connection.

Figure 4A:
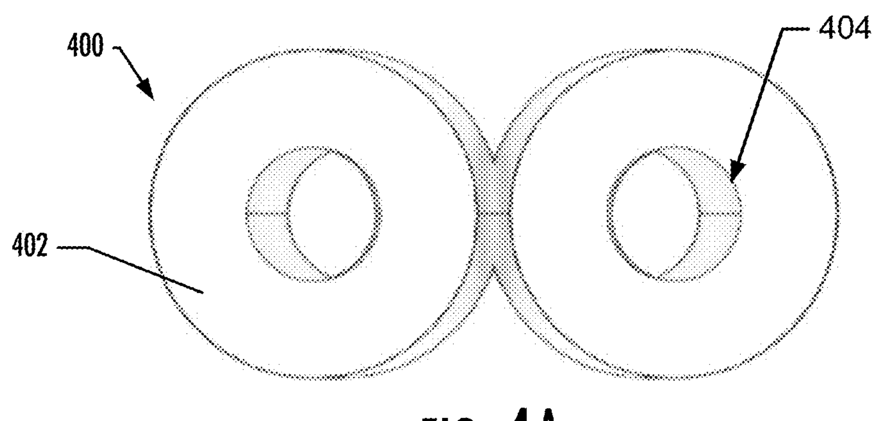
FIGS. 4A, 4B and 4C illustrate a pair of heat shrink tubes, according to some example implementations.
Figure 4B:
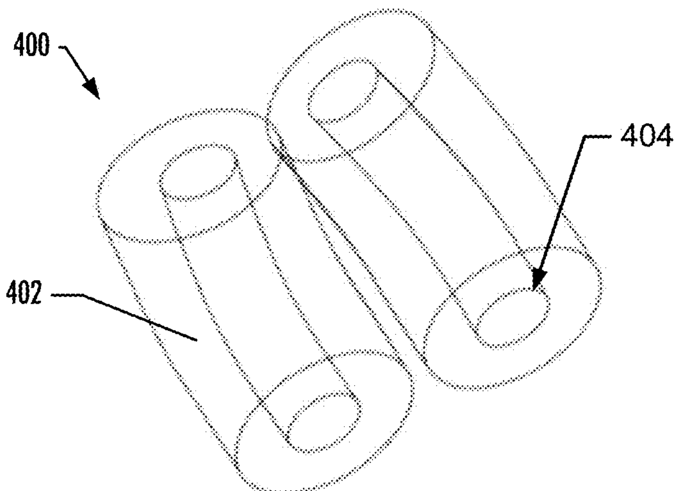
Figure 4C:
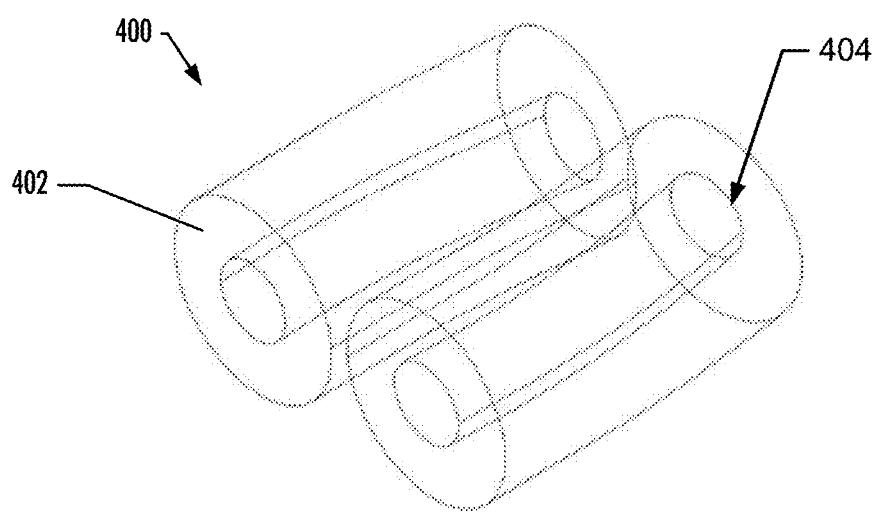

In other examples, an extruded high durometer (yet still somewhat flexible) plastic part and a heat shinkable tube set are added to the subassembly, including a pair of shrink tubes 400, as shown in FIGS. 4A-4C. FIG. 4A shows a front view of the pair of shrink tubes 400, while FIGS. 4B and 4C show transparent, perspective views of the pair of shrink tubes 400. The heat shrink tubes 400, when shrunk to conform to the shape of the underlying components (e.g., the leadwire 206, a distal end of the leadwire 206 and the electrical connections), can provide a layer of insulation around the electrical connections. The layer of insulation may prevent electrical shorts or current leakage between the needle electrode 202 and the leadwire 206.

Moreover, the heat shrink tubes 400 may offer some degree of strain relief, potentially mitigating stress on the electrical connections during manipulation of the assembly. When shrunk, the heat shrink tubes 400 may create a secure mechanical fit around the underlying components. This, in turn, adds rigidity and stability to the subassembly, potentially improving its overall durability. As shown in FIGS. 4A-4C, each heat shrink tube has a cylindrical body 402. The cylindrical body 402 may allow the heat shrink tube to shrink uniformly when exposed to heat, conforming to the contours of the underlying components within the subassembly. The heat shrink tube includes a hole 404 that extends along the longitudinal axis of the cylindrical body 402. The diameter of the hole 404 is designed to accommodate the leadwire 206 after the electrical connections have been formed.

Figure 5A:
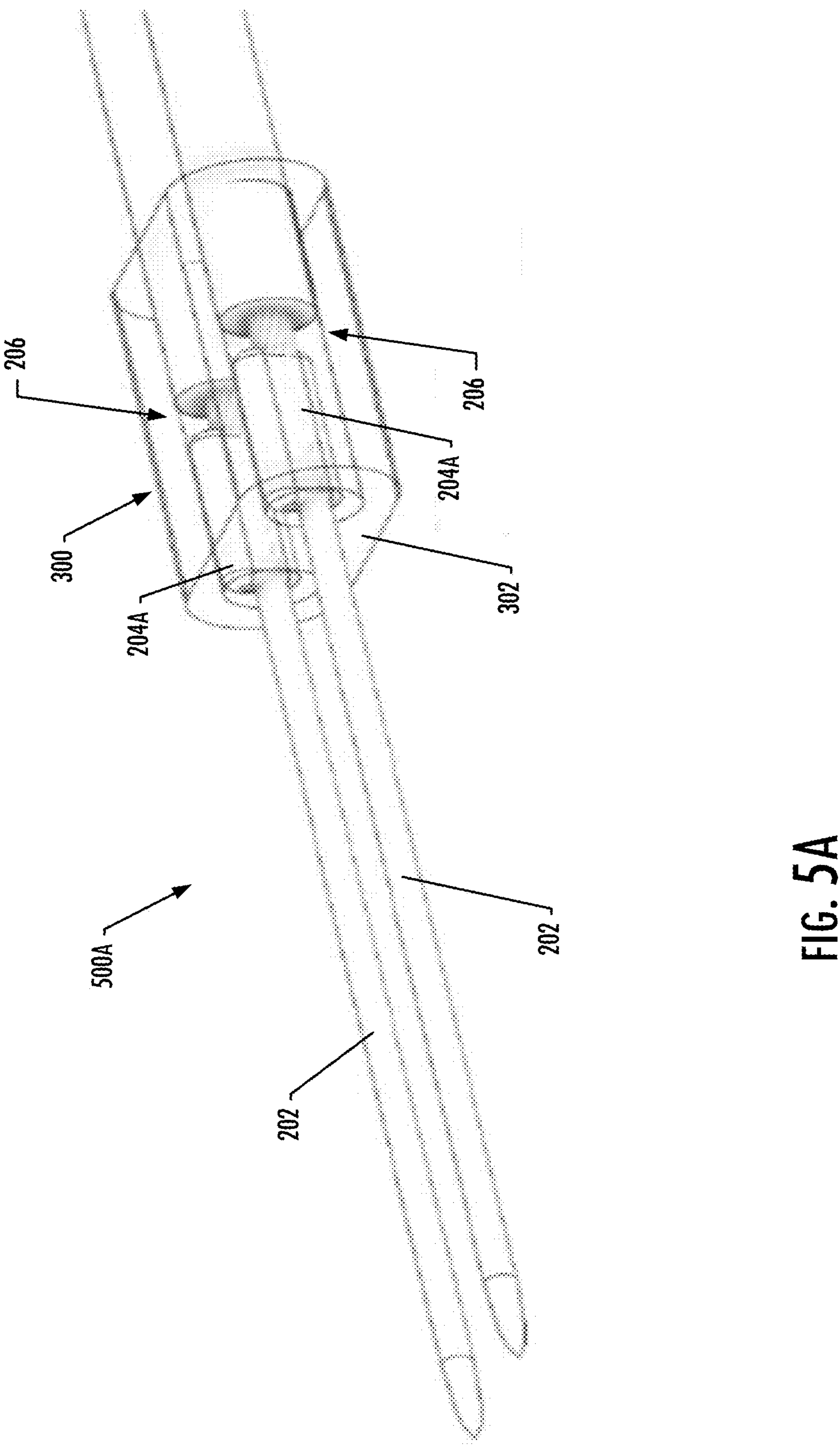
FIGS. 5A, 5B, 5C, 5D, 5E, 5F and 5G illustrate the leadwire spacer coupled to the subassemblies of FIGS. 2A, 2B and 2C, according to some example implementations.
Figure 5B:
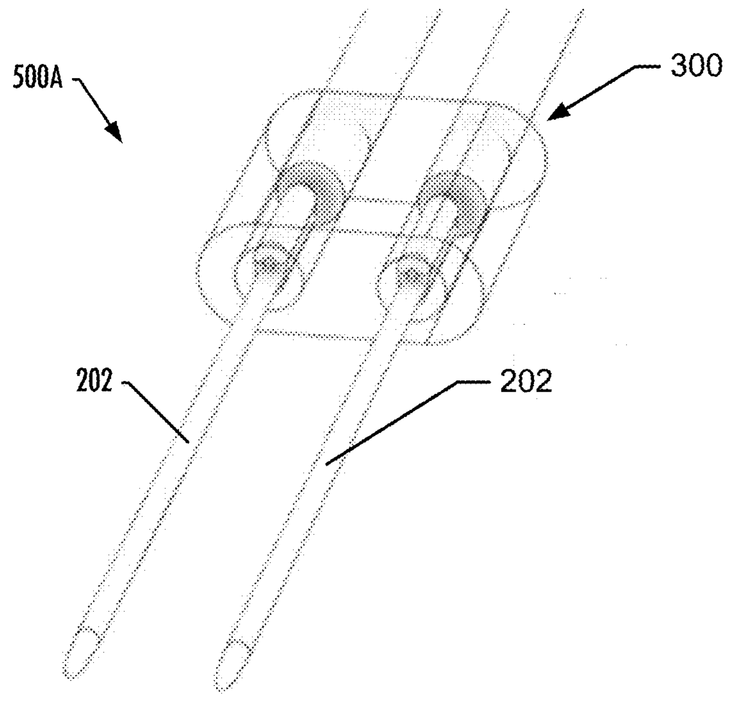
Figure 5C:
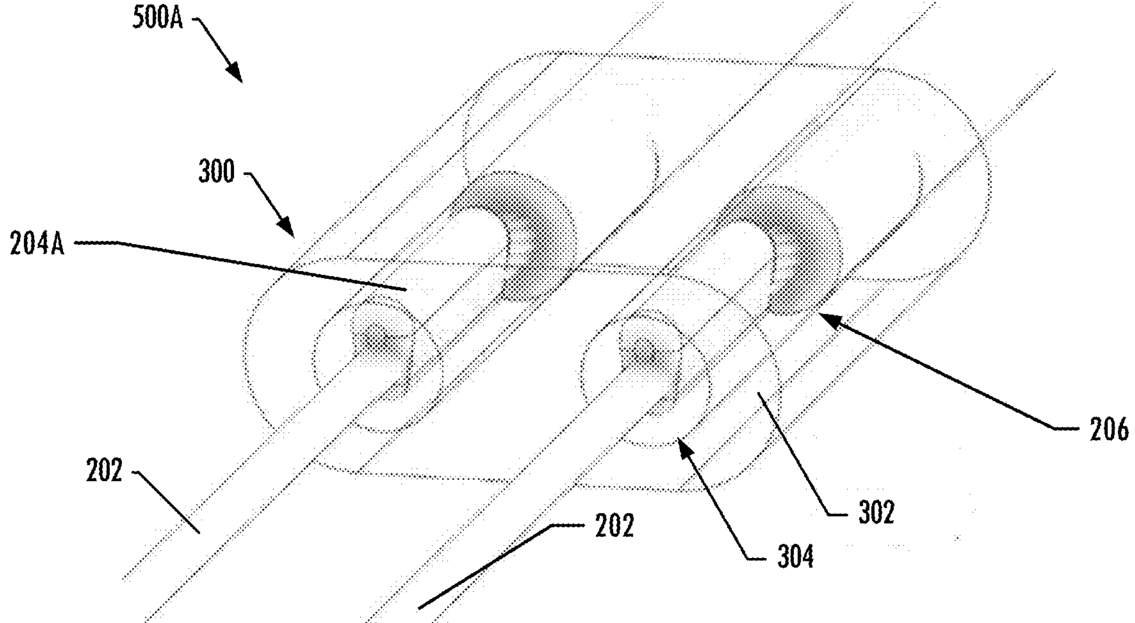

FIG. 5A shows a subassembly 500A where the leadwire spacer 300 is placed over the solder joint 204A and the leadwire 206. FIGS. 5B and 5C show transparent, alternative views of the subassembly 500A. The solder joint 204A may create the electrical connection between the needle electrode 202 and the leadwire 206. The leadwire spacer 300 is positioned to circumferentially surround the electrical connection (e.g., the solder joint 204A), and the distal end of the leadwire 206. The leadwire spacer 300 includes the pair of elongated holes 304 that run parallel to each other along the longitudinal axis of the body 302. The parallel holes 304 are designed to receive the pair of leadwires 206. The leadwire spacer 300 may accommodate a pair of the solder joints 204A, and the distal ends of the pair of leadwires 206 even when they have different diameters.

Figure 5D:
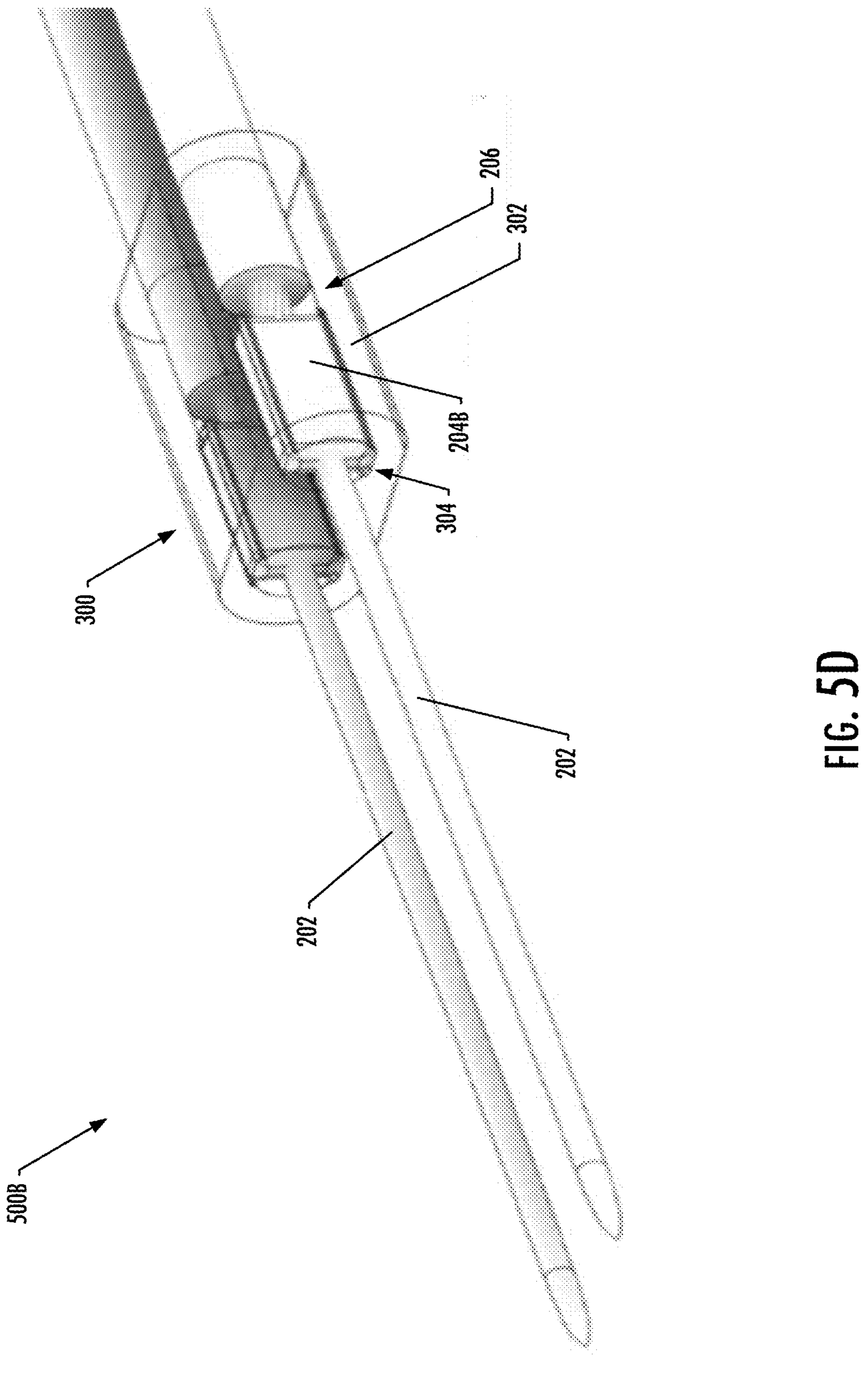
Figure 5E:
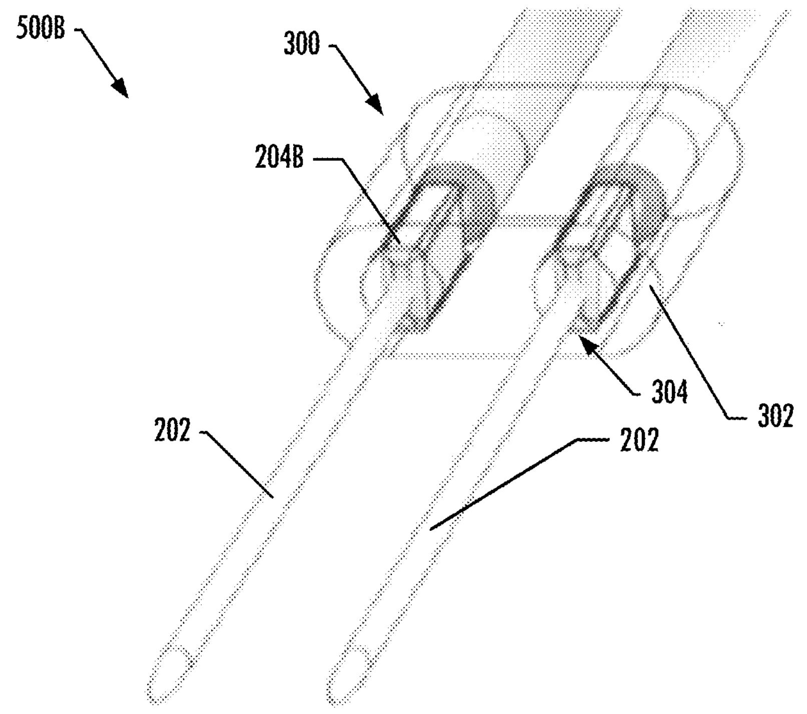
Figure 5F:
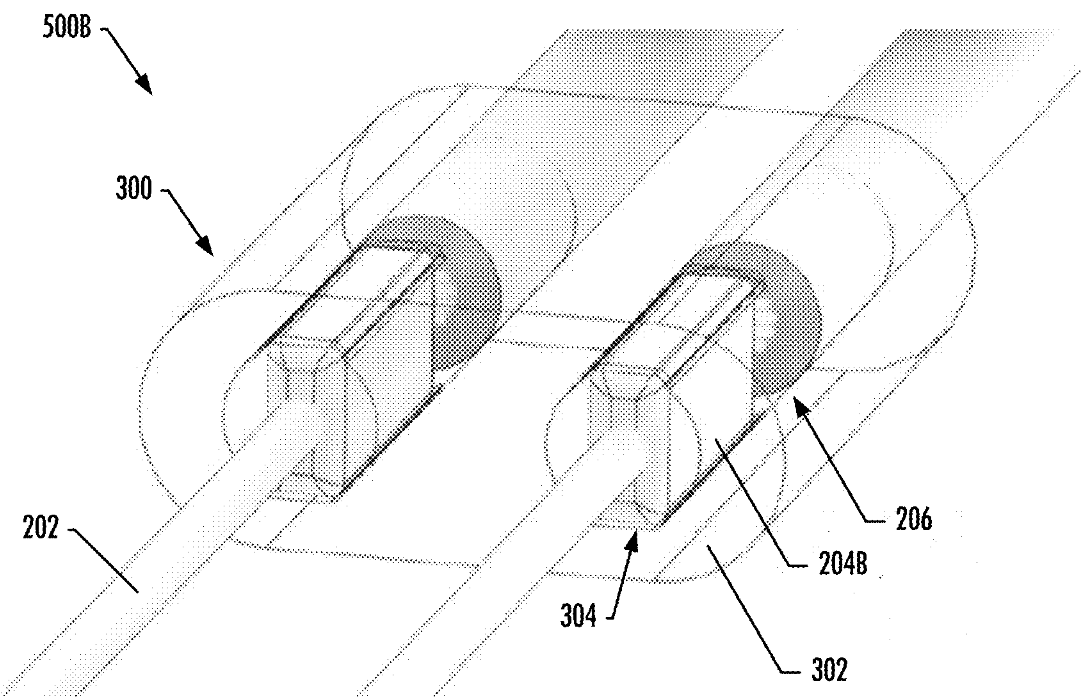

FIGS. 5D-5G show a subassembly 500B which is similar to FIGS. 5A-5C but including the mechanical crimp 204B instead of the solder joint 204A. As shown respectively in FIGS. 5A-5C and 5D-5F, the solder or other connection (mechanical crimp) may be of sufficient size to mechanically deform the two parallel holes 304 in the extruded plastic parts to create additional securement against rotational forces being placed on the needle electrode 202 in the axial direction. In the examples of FIGS. 5D-5F, the mechanical crimp 204B may have an oblong feature. The oblong feature may contribute to the additional securement by mechanically engaging with the holes 304 in the leadwire spacer 300 during the crimping process.

As in FIGS. 5A-5C, the leadwire spacer 300 is positioned to circumferentially surround the mechanical crimp 204B, and the distal end of the leadwire 206 in FIGS. 5D, 5E and 5F. The placement provides structural support and contributes to strain relief. The secure fit of the components within the leadwire spacer 300 may distribute pulling forces on the leadwires more evenly across the mechanical crimp 204B and the spacer body 302, potentially mitigating stress on the connection point during manipulation of the assembly.

Figure 5G:
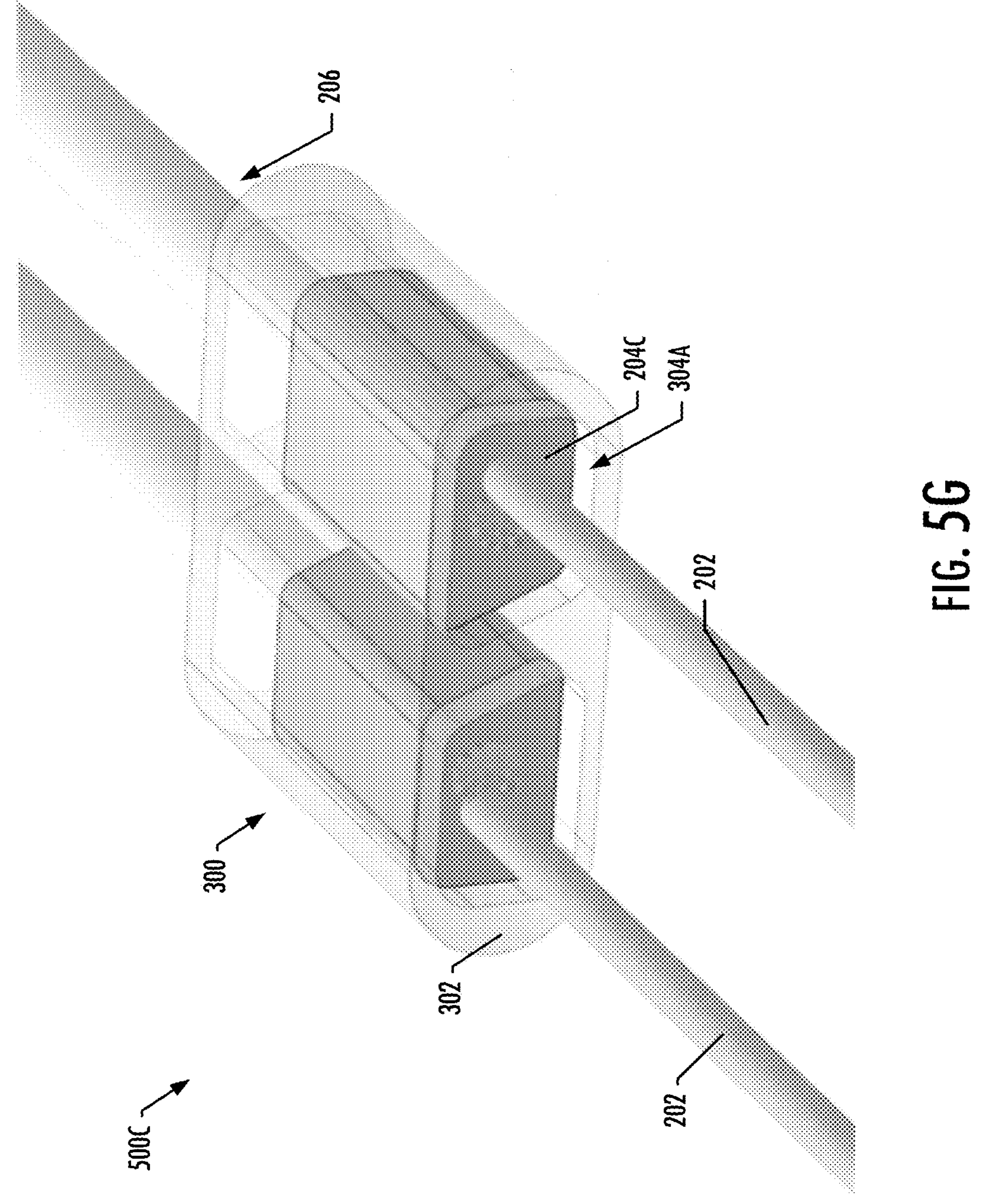

FIG. 5G depicts a subassembly 500C, which uses the conformational crimp 204C for the electrical connection. The mechanical crimp 204C may precisely mate with a correspondingly shaped conformational hole 304A within the leadwire spacer 300. The precise fit between the mechanical crimp 204C and the hole 304A can distribute stress on the connection point more evenly, potentially leading to a stronger and more stable connection. In subassembly 500C, the leadwire spacer 300 may facilitate the secure interlocking connection between the mechanical crimp 204C and the hole 304A. The mechanical crimp 204C may be utilized with or without an adhesive (e.g., cyanoacrylate).

Figure 6A:
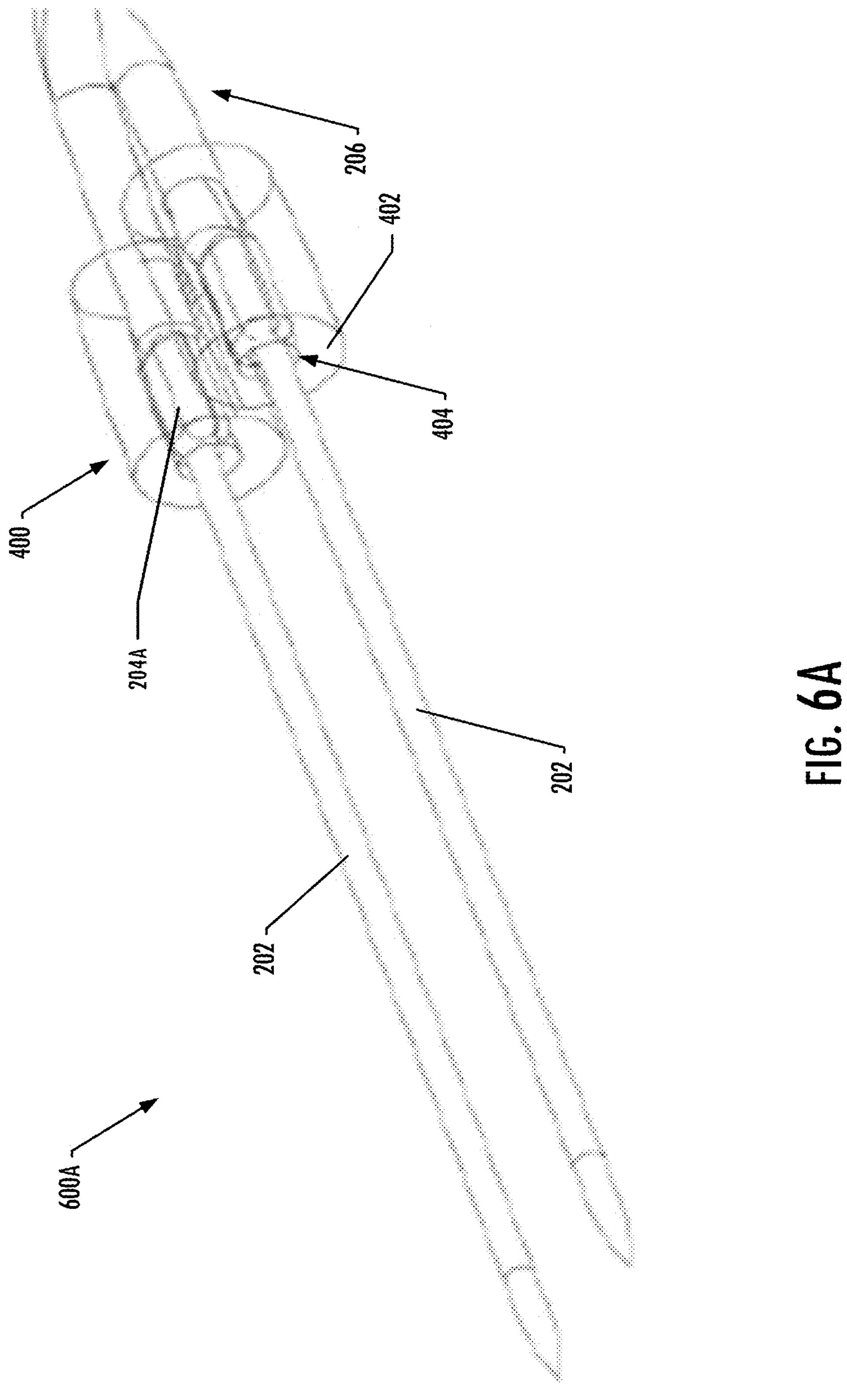
FIGS. 6A, 6B, 6C, 6D, 6E and 6F illustrate the heat shrink tubes coupled to the subassemblies of FIGS. 2A and 2B, according to some example implementations.
Figure 6B:
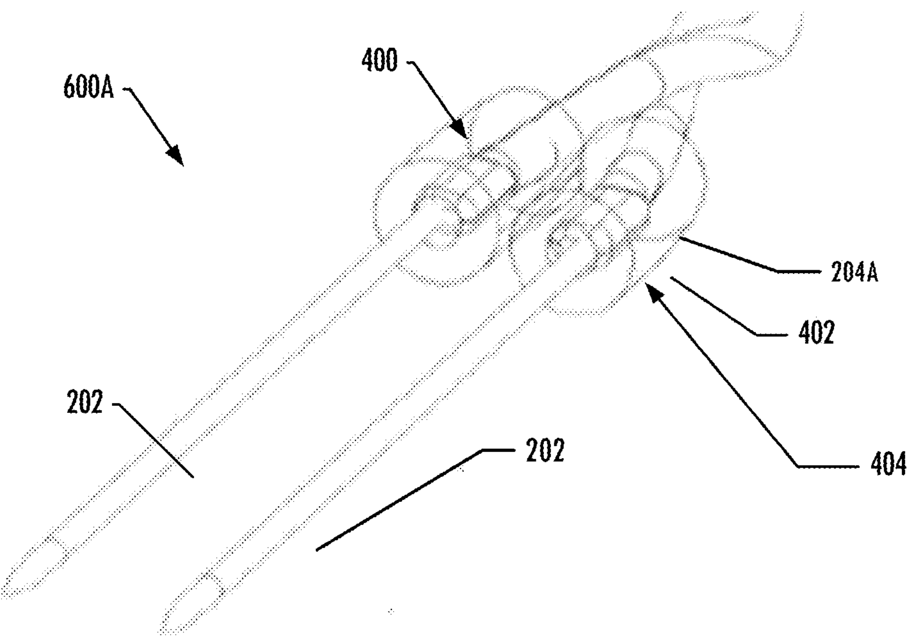
Figure 6C:
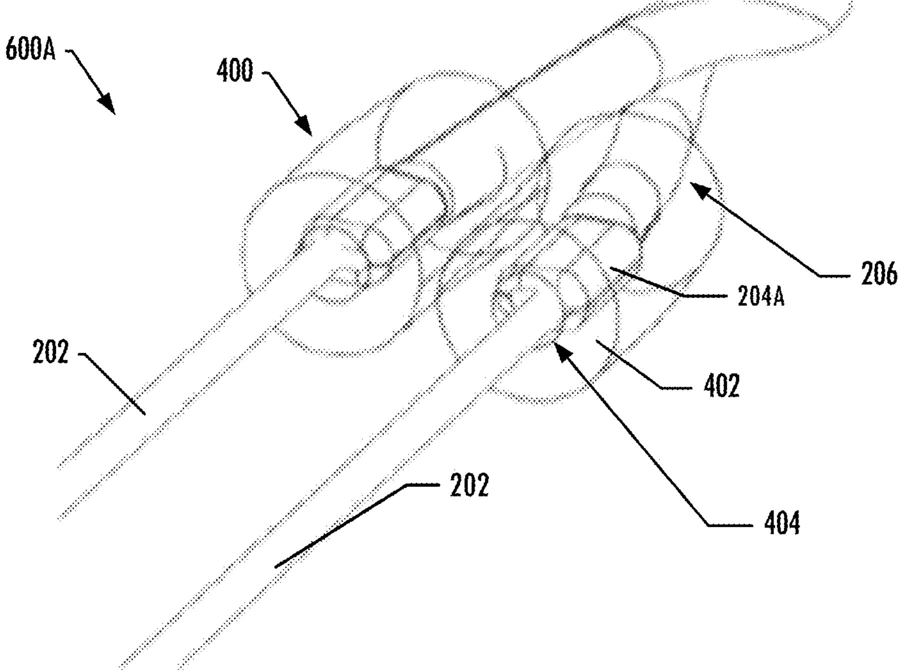

In other examples, FIGS. 6A, 6B and 6C depict a subassembly 600A, which utilizes a heat shrink set 400 for strain relief and environmental protection in conjunction with a solder joint 204A as the electrical connection point. Each of the pair of heat shrink tubes 400 is positioned to circumferentially surround the solder joint 204A, and proximal ends of the leadwire 206. When exposed to heat, each of the pair of heat shrink tubes 400 contracts and conforms to the underlying components, thereby creating a secure fit that distributes pulling forces on the pair of leadwires more evenly. In some examples, the heat may be applied using a heat source (e.g., heat gun) during the manufacturing process. The pair of heat shrink tubes 400 may work as an inner protection layer for the assembly against environmental factors such as dust, moistures and one or more biohazards, contributing to overall longevity of the subassembly 600A.

Figure 6D:
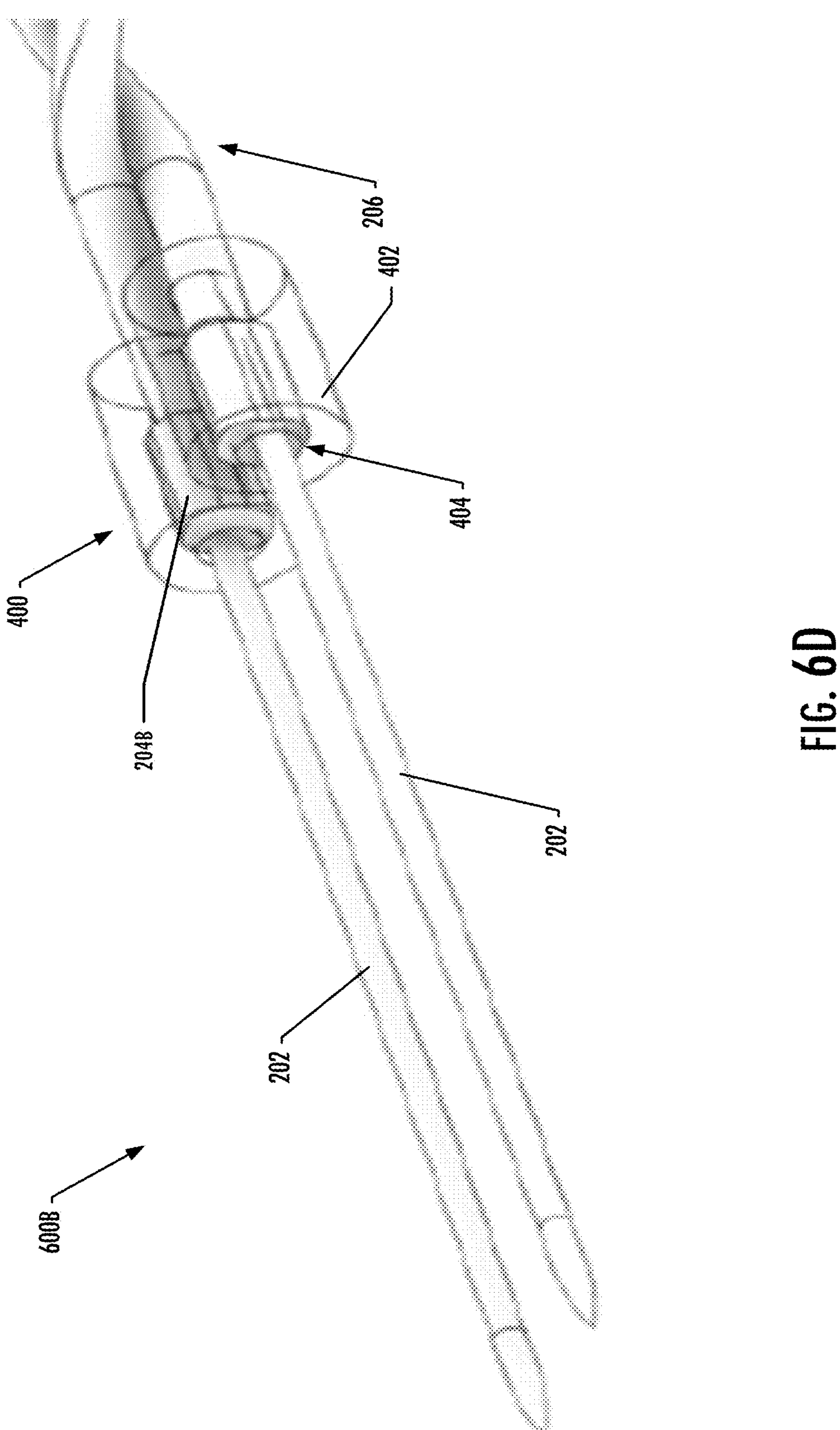
Figure 6E:
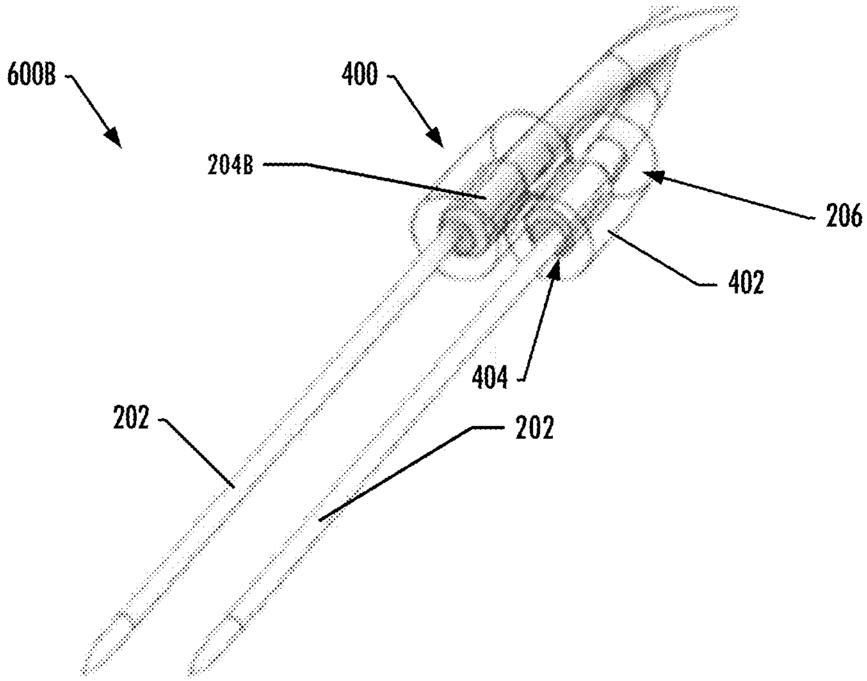
Figure 6F:
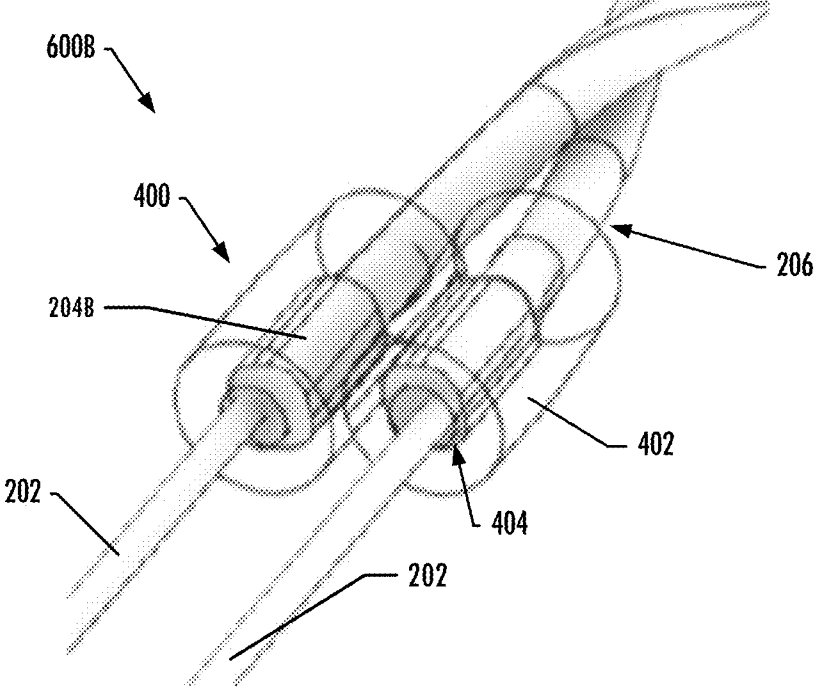

Similarly, FIGS. 6D, 6E and 6F depict a subassembly 600B, which utilizes the pair of heat shrink tubes 400 for strain relief and environmental protection in conjunction with the mechanical crimp 204B as the electrical connection point. Here, the mechanical crimp 204B has a non-circular cross-section (e.g., oval, elliptical, or quadrilateral). Each of the heat shrink tubes 400 is positioned to circumferentially surround the mechanical crimp 204B, and the proximal ends of the leadwire 206. The non-circular cross-section of the mechanical crimp 204B may improve resistance of the needle electrode 202 to rotational forces, particularly when the assembly is bent. This can be especially beneficial during certain procedures. The pair of heat shrink tubes 400 may be utilized with or without an adhesive (e.g., cyanoacrylate).

Figure 7A:
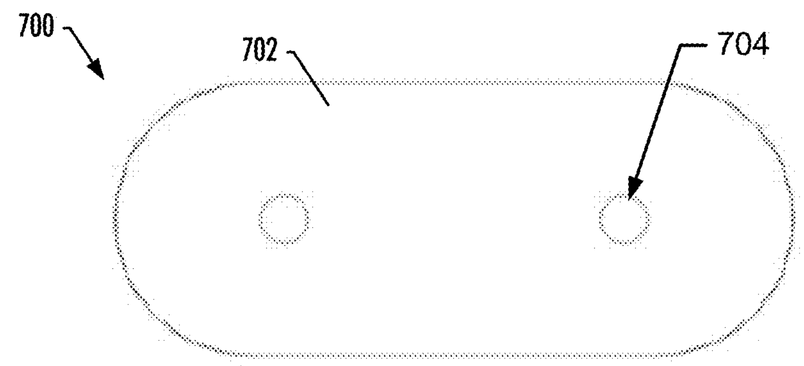
FIGS. 7A, 7B, 7C, 7D and 7E illustrate a needle spacer, according to some example implementations.
Figure 7B:
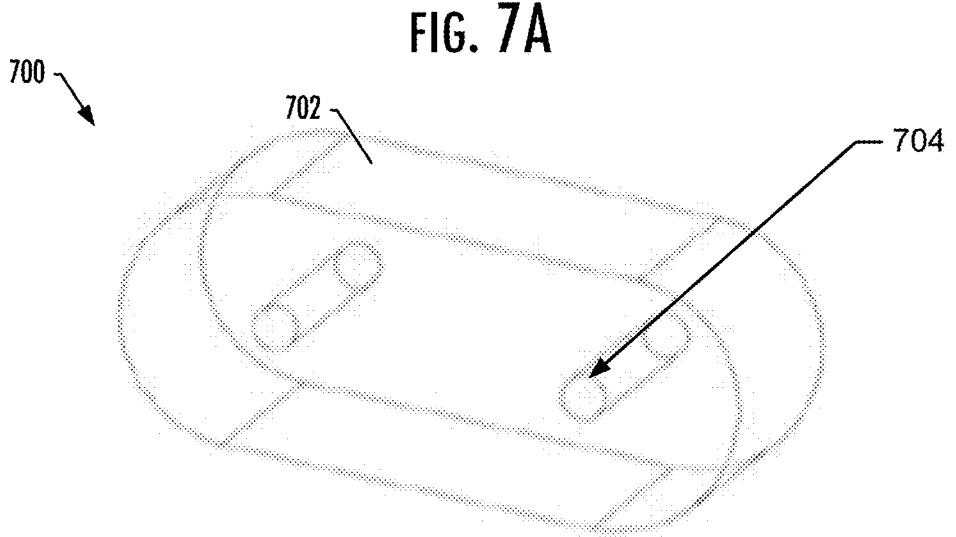
Figure 7C:
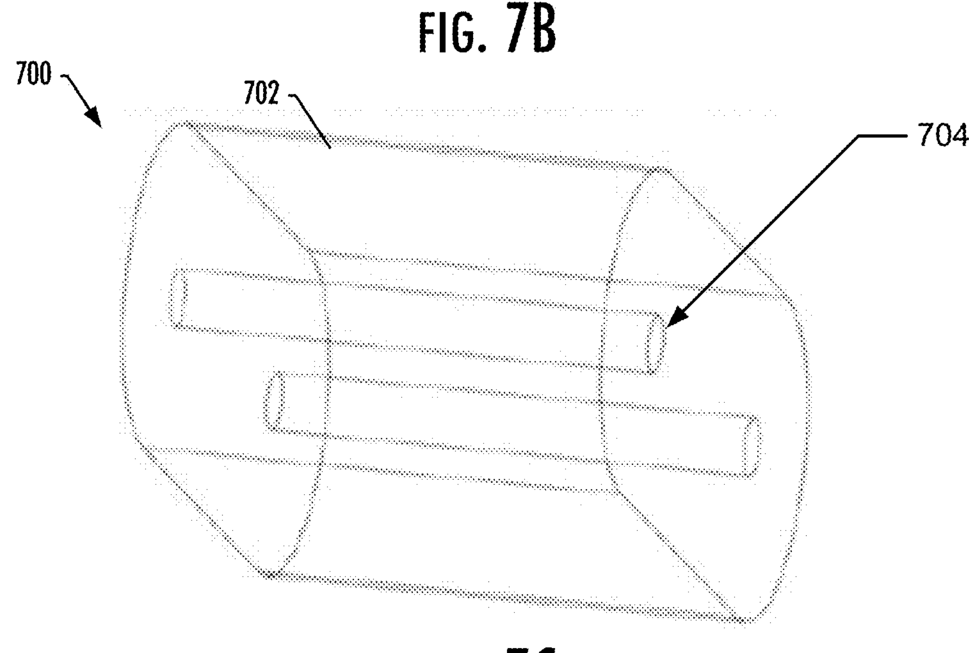
Figure 7D:
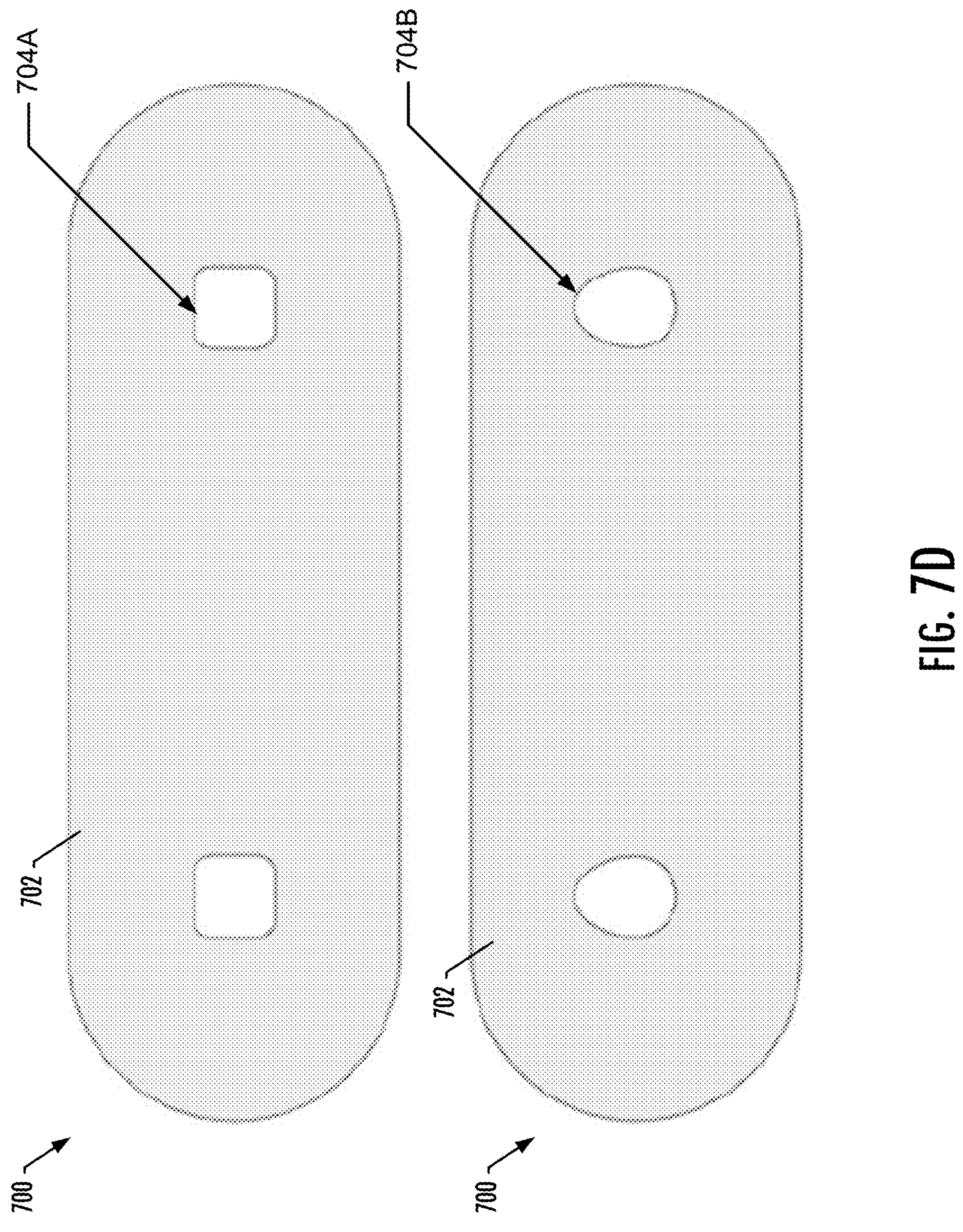
Figure 7E:
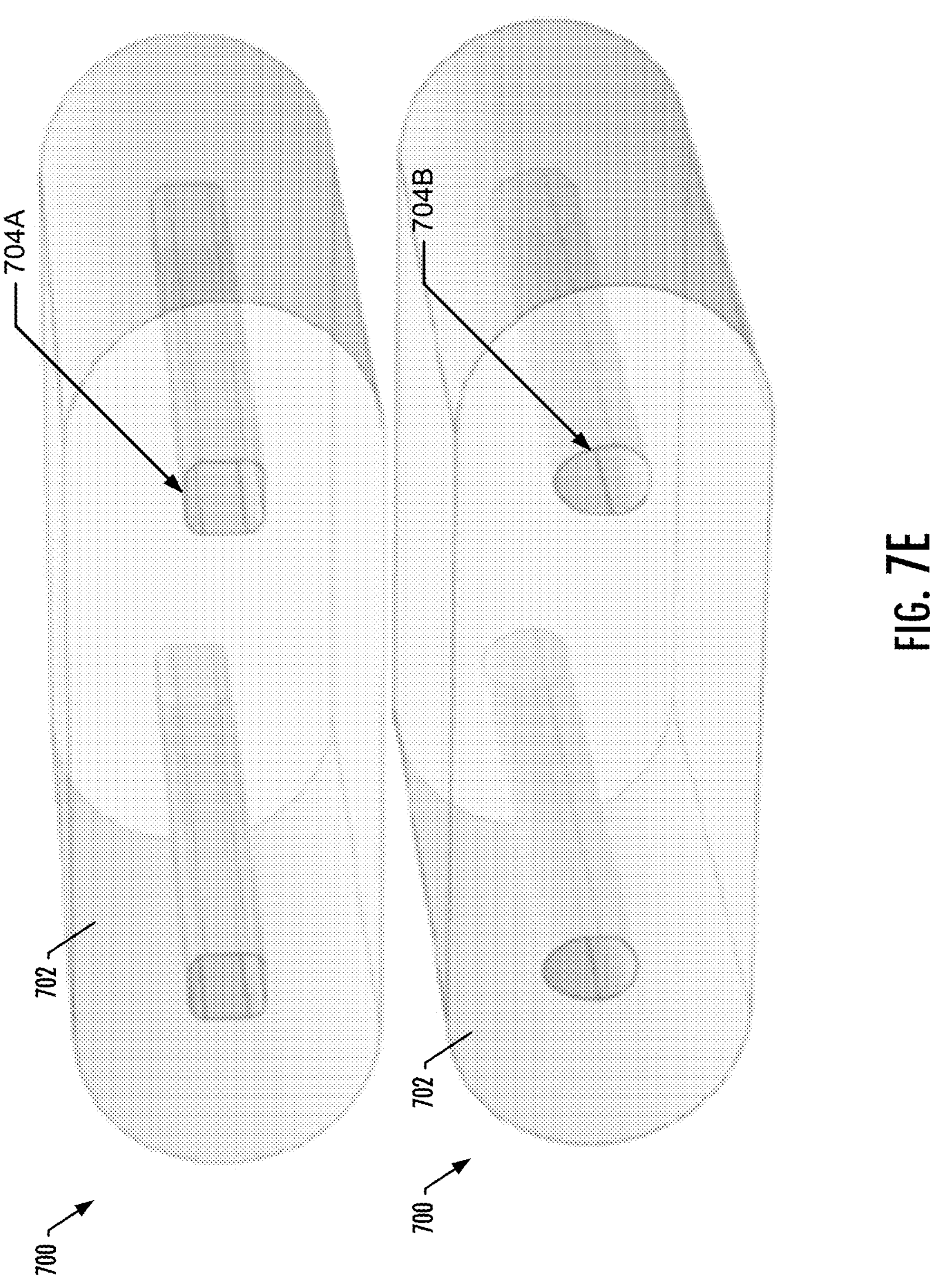

In some examples, the other extruded plastic part is a needle spacer 700 with two parallel holes (which may be circular or non-circular), as shown in FIGS. 7A-7E. FIG. 7A shows a front view of the needle spacer 700, while FIGS. 7B and 7C show transparent, perspective views of the needle spacer 700. Given that a non-loose feel may be desirable, FIGS. 7D and 7E show non-circular holes which fit a wider range of needle diameter sizes than would fit in circular holes. The hole size may be configured to allow the needle spacer 700 to slide onto the two needle electrodes to create a fluid barrier. The hole size may also create a desired inter-needle parallel distancing, thereby facilitating a secure fitting that holds the needle electrodes in a secure position.

The needle spacer 700 may include a body 702. The body 702 may accommodate the parallel holes 704 and potentially interacting with other components within the assembly. The pair of parallel holes 704 are designed to receive the needle electrodes. The parallel holes 704 are positioned in a spaced-apart relationship, defining a spacing between the needle electrodes 202 for improved functionality during use. In some examples, the parallel holes 704 have a circular cross-section. In other examples, the parallel holes 704 have a non-circular cross-section.

The non-circular cross-section of the parallel holes 704 may offer a wider range of compatible needle diameter sizes compared to circular holes. The specific non-circular shapes may include a rectangular shape. The rectangular shaped parallel holes 704A may be suitable to accommodate the needle electrodes with a rectangular cross-section. In other examples, the non-circular cross-section shape may include an oval shape. The oval shaped parallel holes 704B may be suitable to accommodate the needle electrodes of various diameters. The diameter of the parallel holes 704 may be selected such that the needle electrodes slide smoothly into the needle spacer 700 during the assembly and fluid barrier is created between the needle electrodes, thereby reducing risk of cross-contamination. The size of the parallel holes may establish a defined inter-needle parallel distancing. The needle spacer 700 may be an extrusion with a fixed cross-sectional profile, hence referred to as a "front plastic extrusion." The needle spacer 700 may have a pre-defined shape for the body 702 and the parallel holes 704 along its length.

Figure 8A:
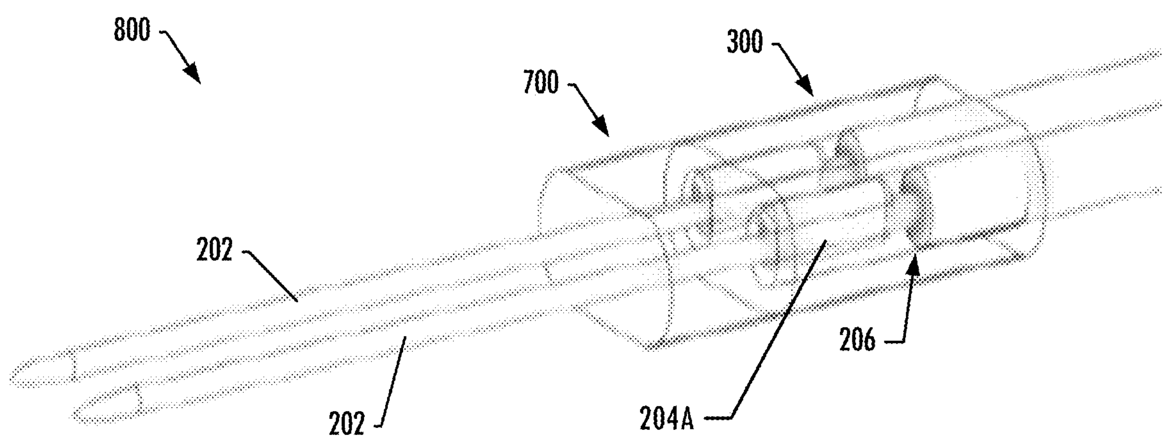
FIGS. 8A and 8B illustrate a needle spacer in abutment with a leadwire spacer, according to some example implementations.
Figure 8B:
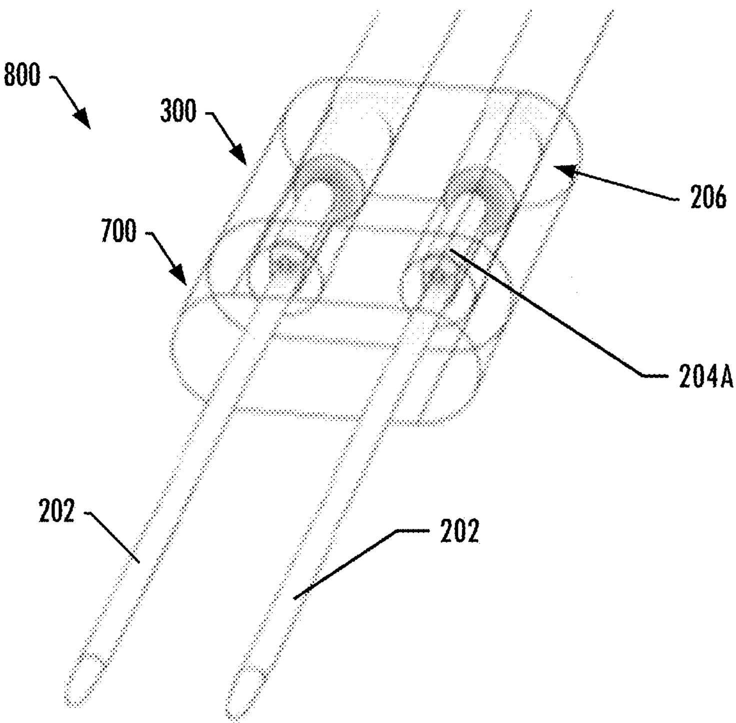

FIG. 8A shows a subassembly 800 in which the needle spacer 700 is placed adjacent to and abutting the leadwire spacer 300. FIG. 8B shows an alternative view of FIG. 8A. Similar to the needle spacer 700, the leadwire spacer 300 may be an extrusion with a fixed cross-sectional profile, hence referred to as a "back plastic extrusion." In these examples, the outer shapes of the front and back plastic extrusions are identical, thereby allowing a seamless outer profile when in abutment. In some examples, there is a space gap between the abutting surfaces of the needle spacer 700 and the leadwire spacer 400. In other examples, there is no spacer gap between the abutting surfaces.

When the needle spacer 700 and the leadwire spacer 300 are positioned next to each other, surfaces of these extrusions come into direct contact, creating the abutment. In some examples, the entire opposing faces of the needle spacer 700 and the leadwire spacer 300 may be in direct contact, eliminating the spacer gap between them, which increases the surface area for a strong connection. In other examples, one or more designated contact points on the opposing faces of the spacers 700 and 300 create the abutment. The designated contact points may be placed to provide stability even decreasing the spacer gap between some portions of the opposing faces. Both the needle spacer 700 and the leadwire spacer 300 are aligned and oriented along the longitudinal axis of the assembly. The spacers are positioned in a straight line along the length of the assembly, contributing to its overall stability and functionality.

Figure 9A:
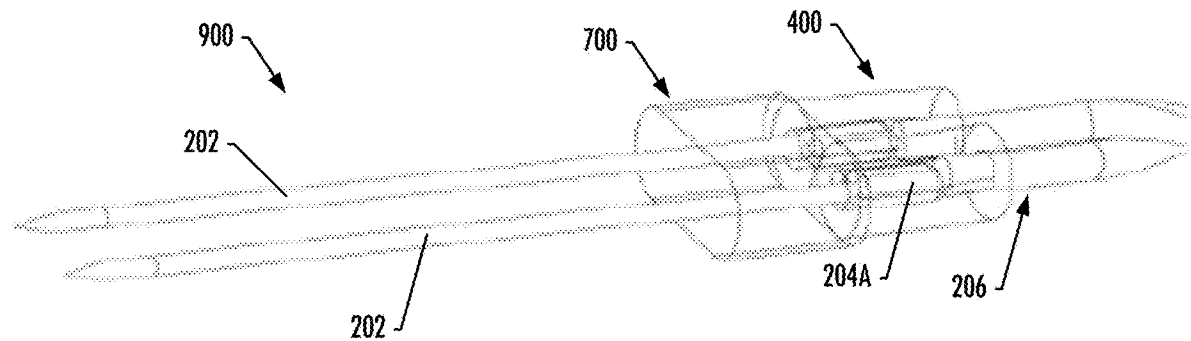
FIGS. 9A and 9B illustrate a needle spacer in abutment with the heat shrink tubes, according to some example implementations.
Figure 9B:
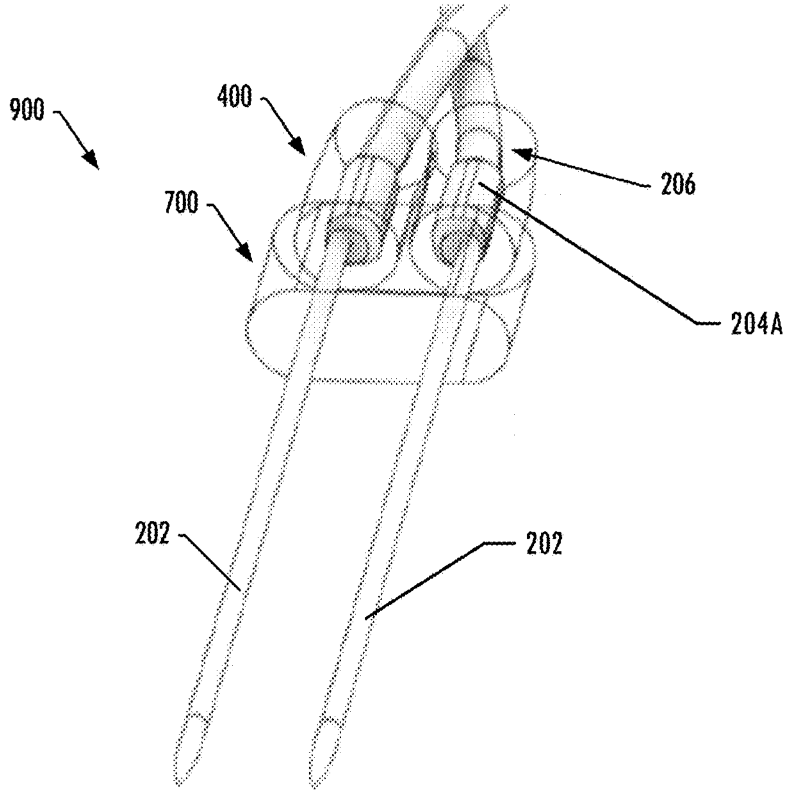

FIG. 9A shows a subassembly 900 in which the needle spacer 700 is placed adjacent to and abutting the pair of shrink tubes 400. FIG. 9B shows an alternative view of FIG. 9A. The subassembly 900 is distinct compared to the subassembly 800 of FIGS. 8A and 8B. The pair of heat shrink tubes 400 may include two separate heat shrink tubes. These tubes may be positioned to cover specific areas within the assembly. The needle spacer 700 is a single extruded component. When the subassembly 900 is put together, the two separate heat shrink tubes may cover the electrical connections (solder joints 204A or mechanical crimps 204B and 204C) between the needle electrodes and the leadwires, and the proximal ends of the leadwires, and optionally an outer surface portion of the needle spacer 700.

Figure 10:
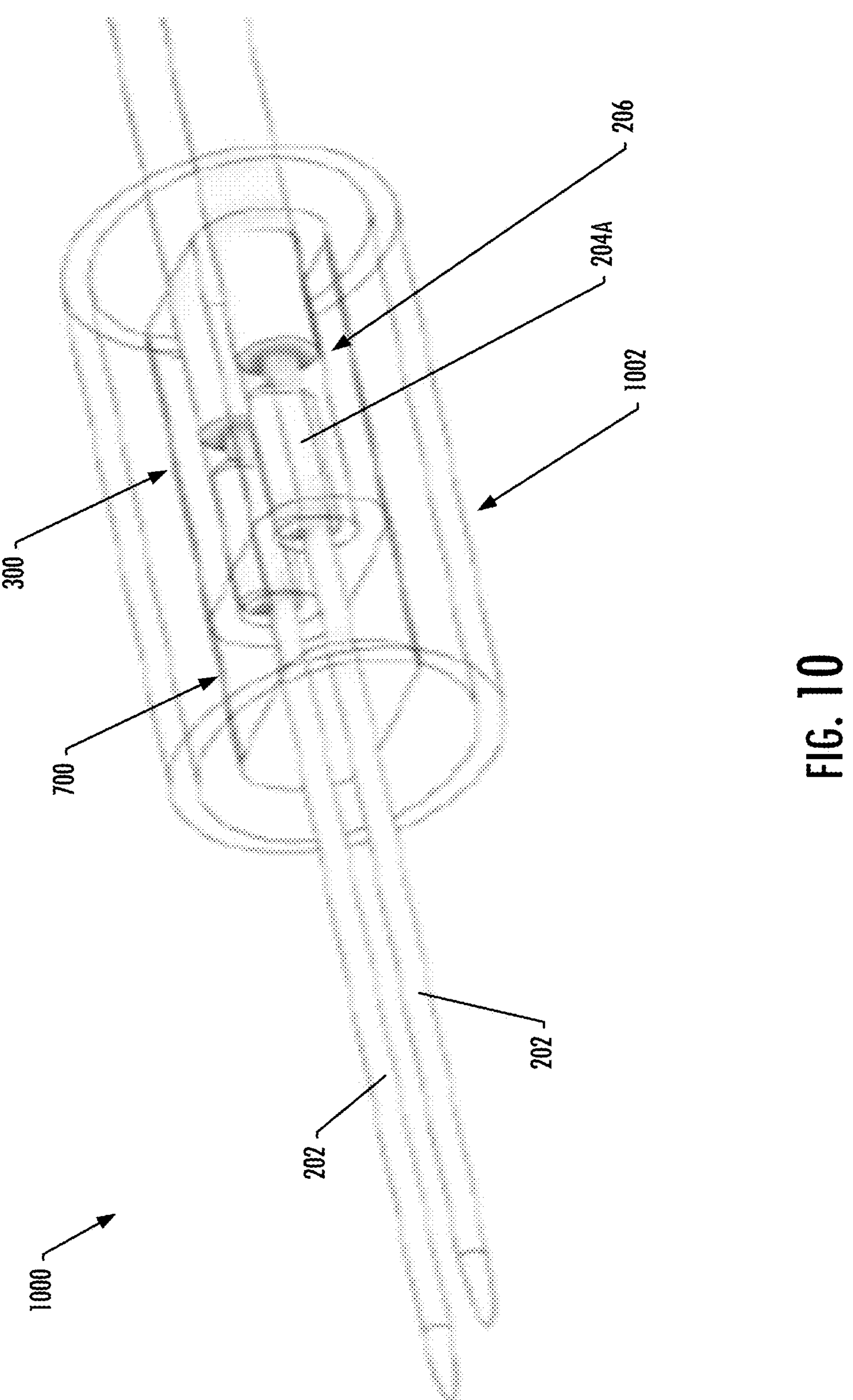
FIG. 10 illustrates the placement of thermoplastic shrinkable tubing over the needle spacer and leadwire spacer, according to some example implementations.
Figure 11A:
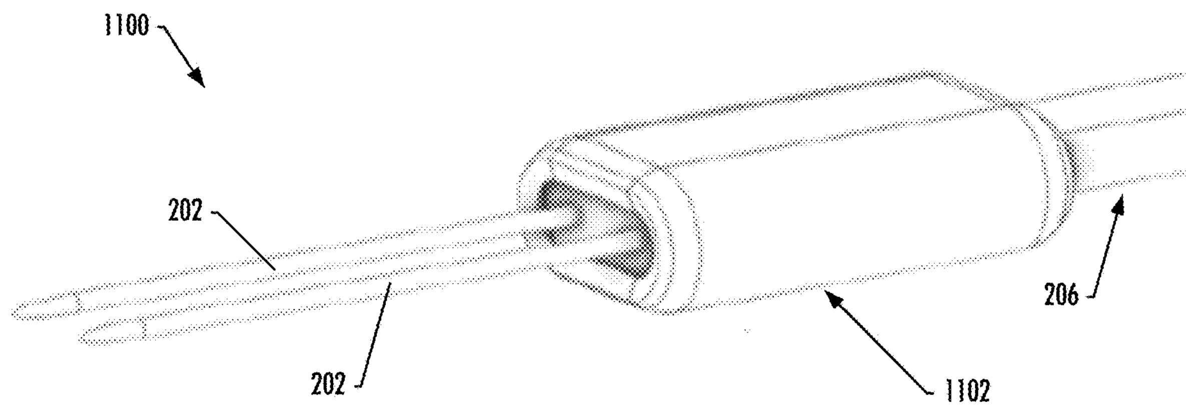
FIGS. 11A and 11B illustrate a neurodiagnostic needle electrode pair utilizing a needle spacer and a leadwire spacer, according to some example implementations.
Figure 11B:
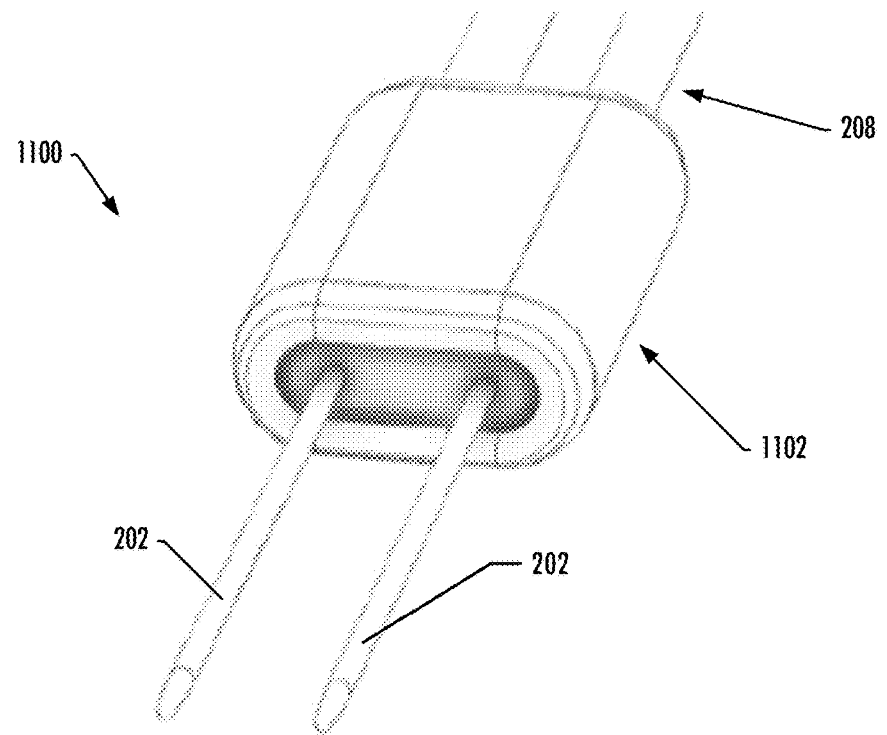

In some examples, a thermoplastic shrinkable tubing (heat shrink tube 1002) is placed (unrecovered) over the two extruded plastic parts 700 and 300, as shown in a subassembly 1000 of FIG. 10. In these examples, when the heat shrink tube 1002 is recovered (i.e., shrank), the combination of the two plastic extrusions 700 and 300, and the recovered heat shrink tube 1102 form what amounts to a solid unit (i.e., a hub) with limited flexibility and functionally equivalent in form factor to an injection molded hub. FIGS. 11A and 11B show perspective views of a neurodiagnostic needle electrode pair assembly 1100 where the recovered heat shrink tube 1102 is over the extruded plastic parts 700 and 300, and forming a hub. In these examples, the outer shapes of the extruded plastic parts facilitate consistent heat shrink seal integrity due in part to their semicircular shapes, as well as their identical outer dimensions. The resultant hub thereby appears unibody in its construction.

Figure 12:
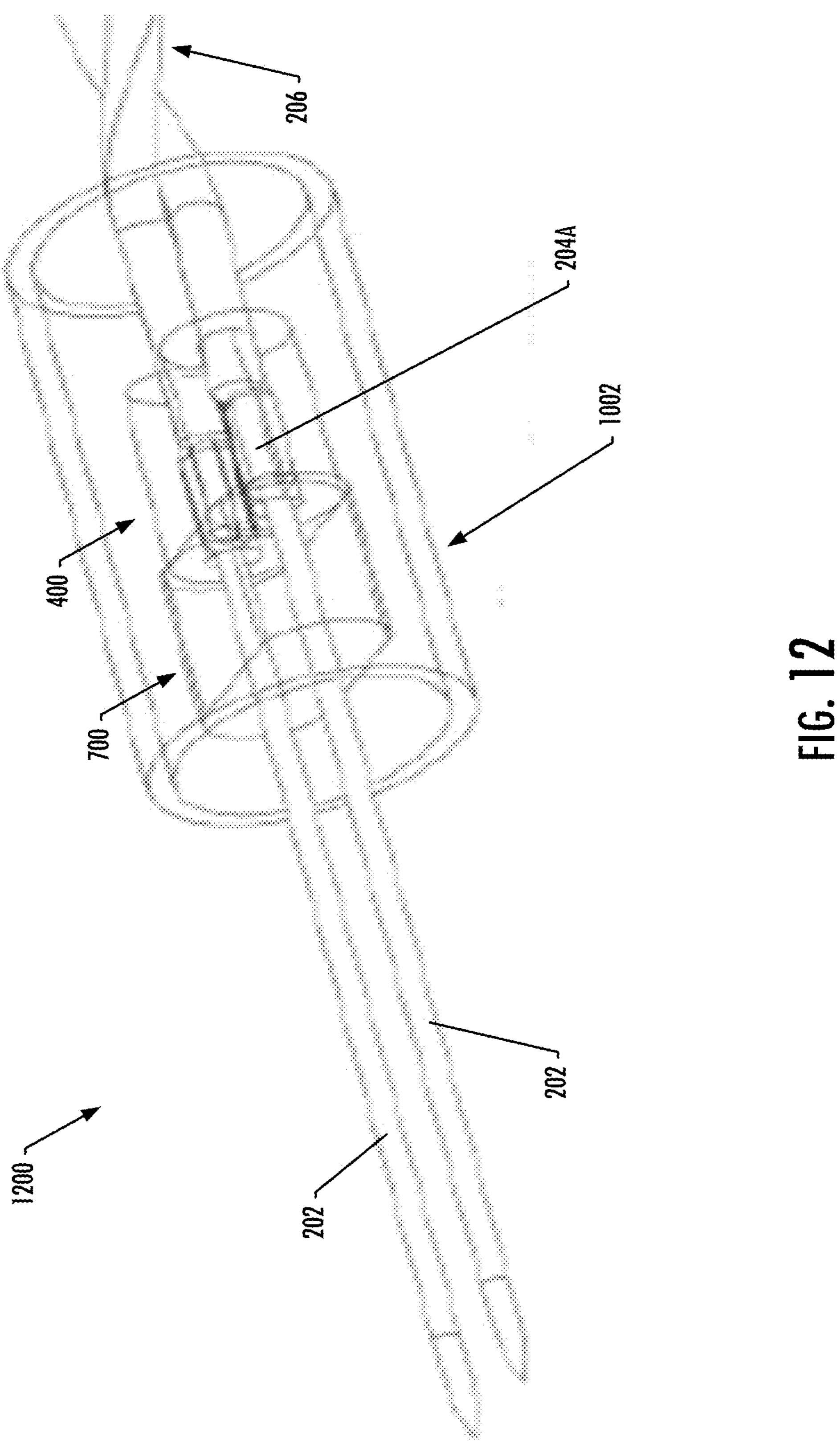
FIG. 12 illustrates the placement of thermoplastic shrinkable tubing over the needle spacer and the heat shrink tubes, according to some example implementations.
Figure 13A:
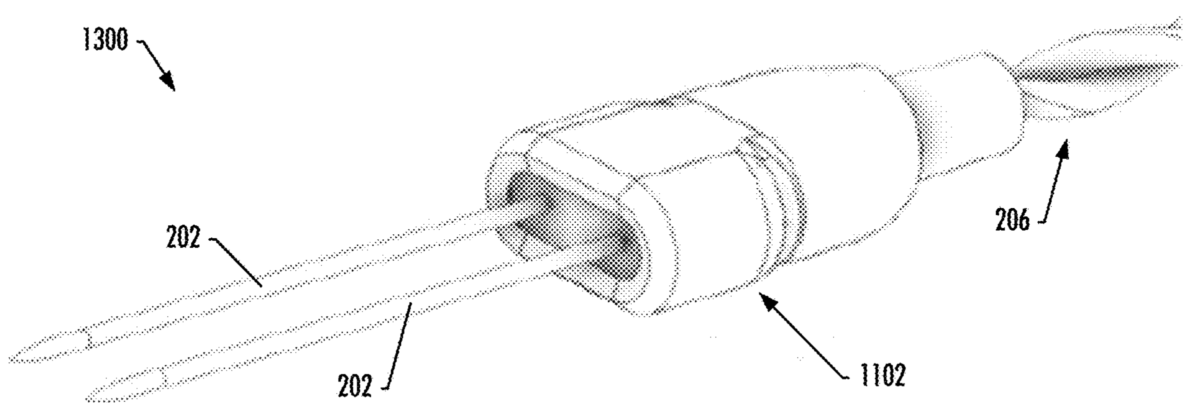
FIGS. 13A and 13B illustrate a neurodiagnostic needle electrode pair utilizing a needle spacer and a pair of heat shrink tubes, according to some example implementations.
Figure 13B:
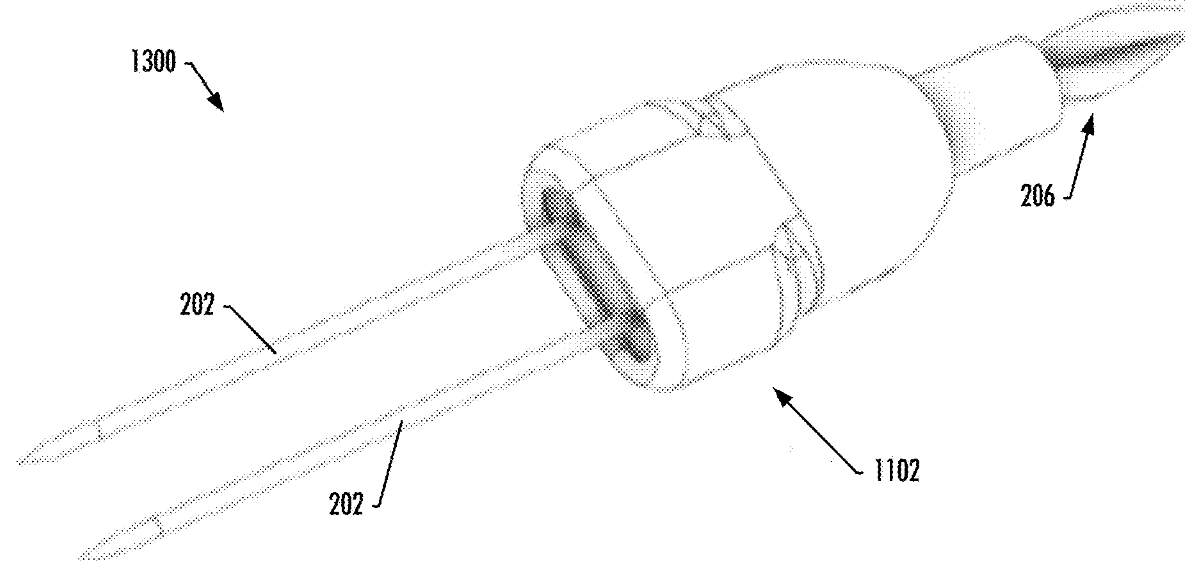

In other examples, a thermoplastic shrinkable tubing (heat shrink tube 1002) is placed (unrecovered) over the needle spacer 700 and the pair of tubes 400, as shown in subassembly 1200 of FIG. 12. In some example implementations, an adhesive-lined heat shrink tube may be used. The adhesive lining may include a thin layer of adhesive material applied to an inner surface of the heat shrink tube 1002. When heat is applied to recover (shrink) the heat shrink tube 1002, the adhesive lining is activated and transitions to a liquid state. As the heat shrink tube tightly conforms to the outer surfaces of the needle spacer 700 and the pair of tubes 400, the melted adhesive flows and fills any gaps between the components. Upon cooling, the adhesive hardens, creating a strong bond that enhances the strain relief properties and environmental protection of the neurodiagnostic needle electrode pair assembly 1300 shown in FIGS. 13A and 13B. This strong bond can further improve the resistance of the needles to spin when in a bent configuration and enhance the fluid resistance of the assembly.

Figure 14:
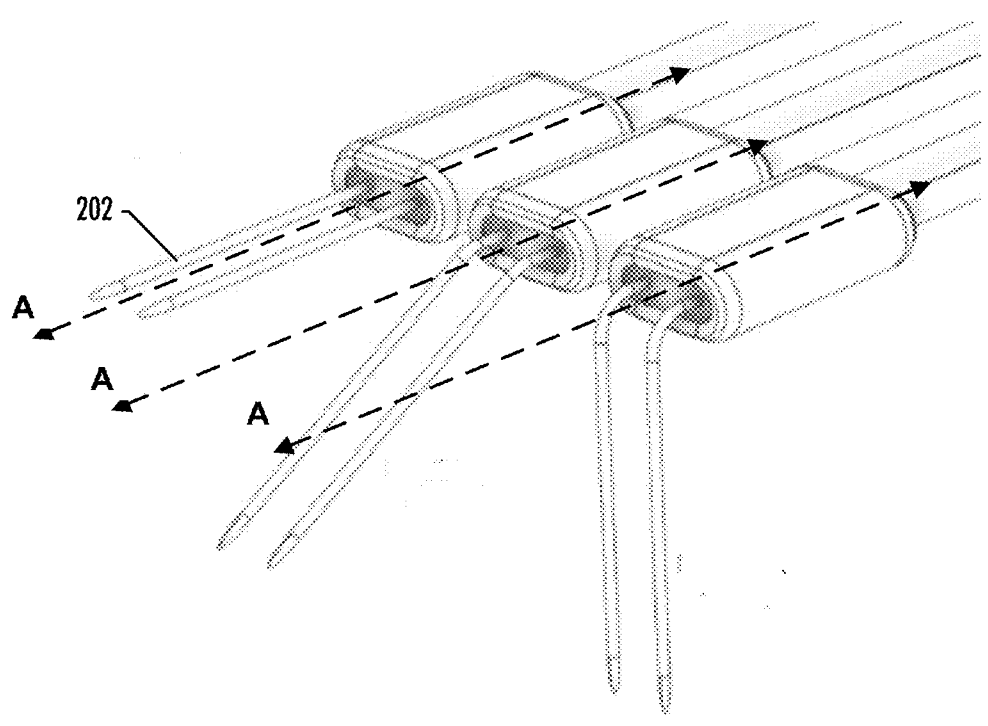
FIGS. 14 and 15 illustrate various needle positions of a neurodiagnostic needle electrode pair, according to some example implementations.
Figure 15:
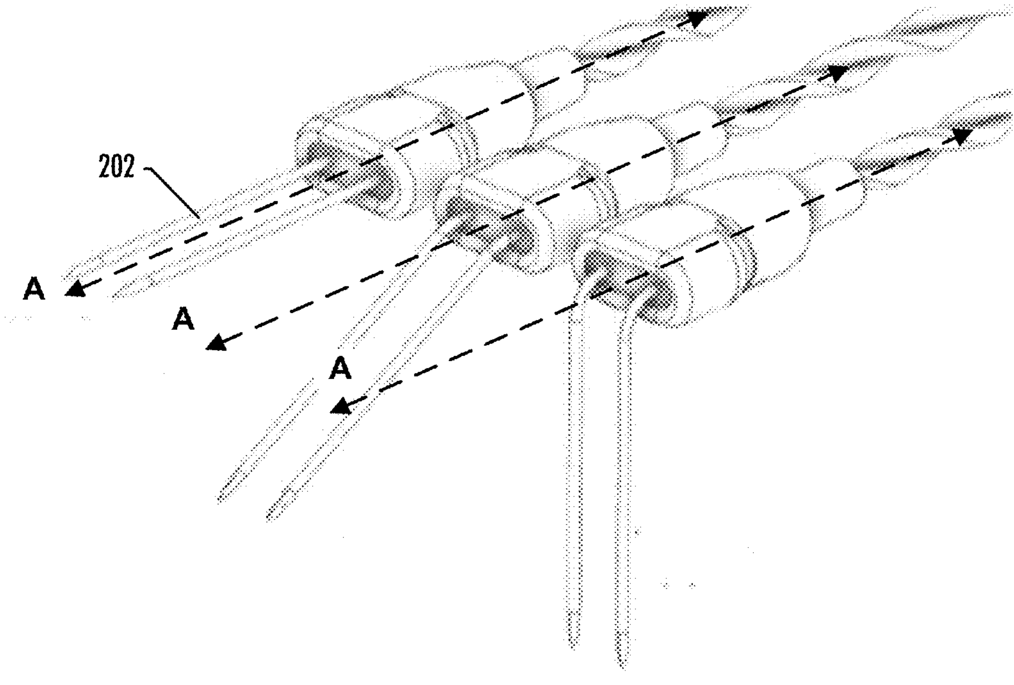

In some examples, as shown in FIGS. 14 and 15, the needle electrodes used in the neurodiagnostic needle electrode pair assembly may be bent rather than straight. FIGS. 14 and 15 show that the needle electrodes may be bent at various angles. FIG. 14 shows a plurality of assemblies disclosed in the FIGS. 11A and 11B, in which the recovered heat shrink tube 1102 covers the needle spacer 700 and the leadwire spacer 300. Whereas, FIG. 15 shows a plurality of assemblies disclosed in FIGS. 13A and 13B, in which the recovered heat shrink tube 1102 covers the needle spacer 700 and the pair of recovered heat shrink tubes 400. The needle electrodes may be oriented at a predetermined angle relative to a longitudinal axis A. The predetermined angle may range from 0 to 90 degrees.

Figure 16:
FIG. 16 is a flowchart illustrating various steps in a method of forming a neurodiagnostic needle electrode pair assembly shown in FIGS. 11A and 11B, according to some example implementations.
Figure 16:
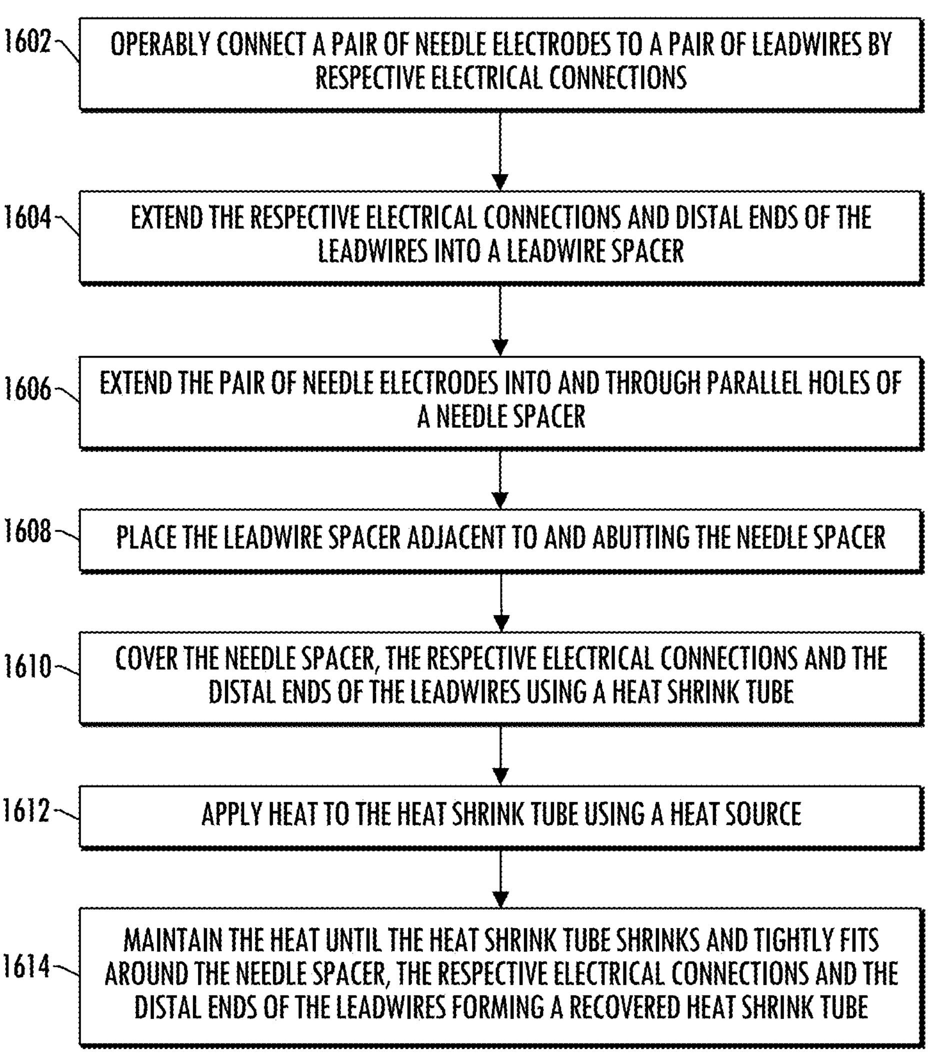

FIG. 16 illustrates a method 1600 of manufacturing a neurodiagnostic needle electrode pair assembly 1100 utilizing a needle spacer 700 in abutment with a leadwire spacer 300, according to some example implementations. As shown at block 1602, the method may include operably connecting a pair of needle electrodes to a pair of leadwires by respective electrical connections. The method may include extending the respective electrical connections and distal ends of the leadwires into a leadwire spacer 300, as shown at block 1604. The method may include extending the pair of needle electrodes into and through parallel holes of the needle spacer 700, as shown at block 1606. The method may include placing the leadwire spacer 300 adjacent to and abutting the needle spacer 700, as shown at block 1608.

The method 1600 may include covering the needle spacer 700, the respective electrical connections and the distal ends of the leadwires using a heat shrink tube 1002, as shown at block 1610. The method may include applying heat to the heat shrink tube 1002 using a heat source, as shown at block 1612. The method may include maintaining the heat until the heat shrink tube 1002 shrinks and tightly fits around the needle spacer 700, the respective electrical connections and the distal ends of the leadwires forming a recovered heat shrink tube 1102, as shown at block 1614.

Figure 17A:
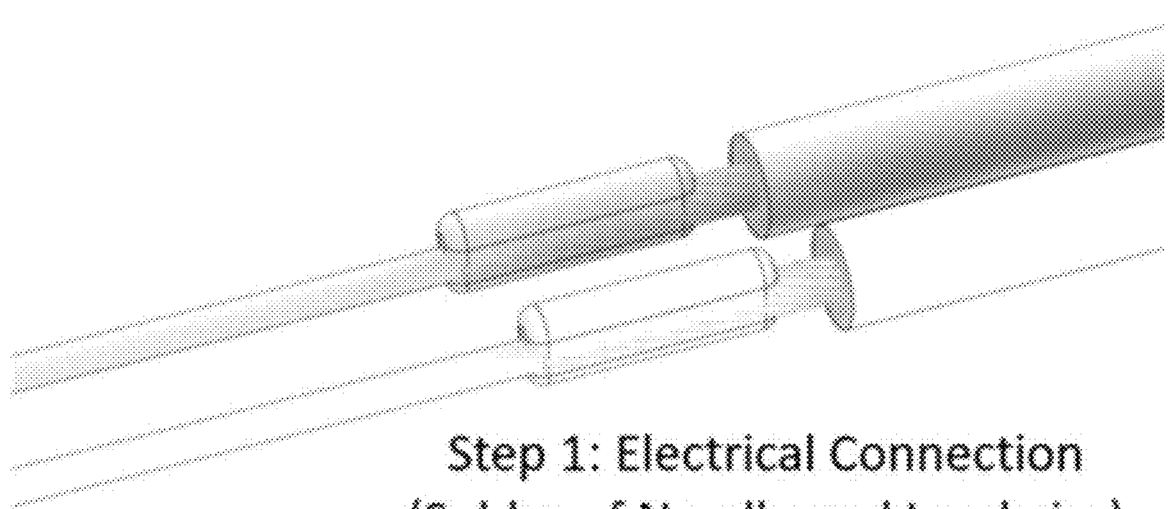
FIGS. 17A, 17B, 17C and 17D illustrate a process of forming the neurodiagnostic needle electrode pair utilizing a needle spacer and a leadwire spacer shown in FIGS. 11A and 11B, according to some example implementations.
Figure 17B:
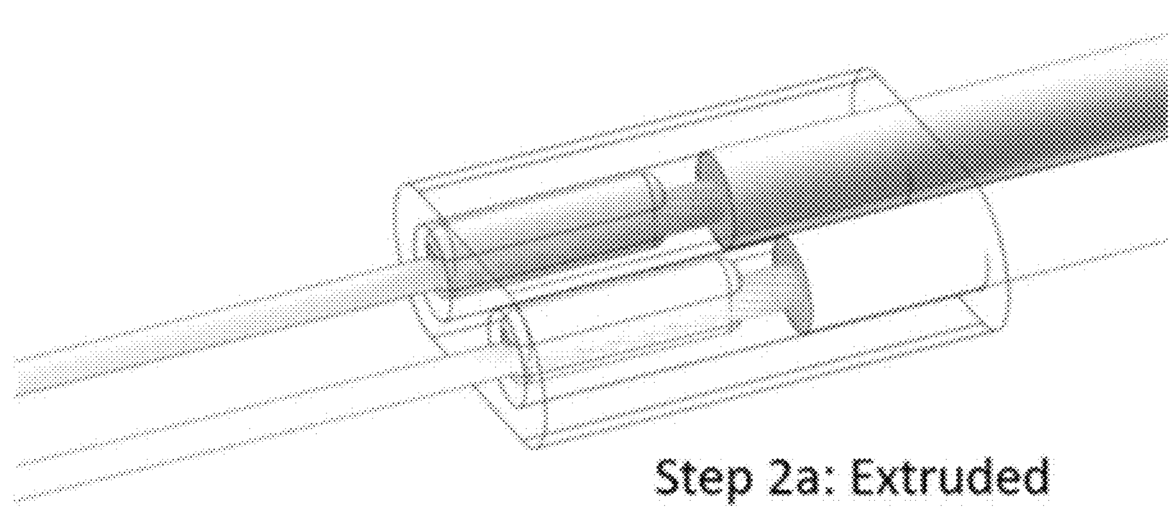
Figure 17C:
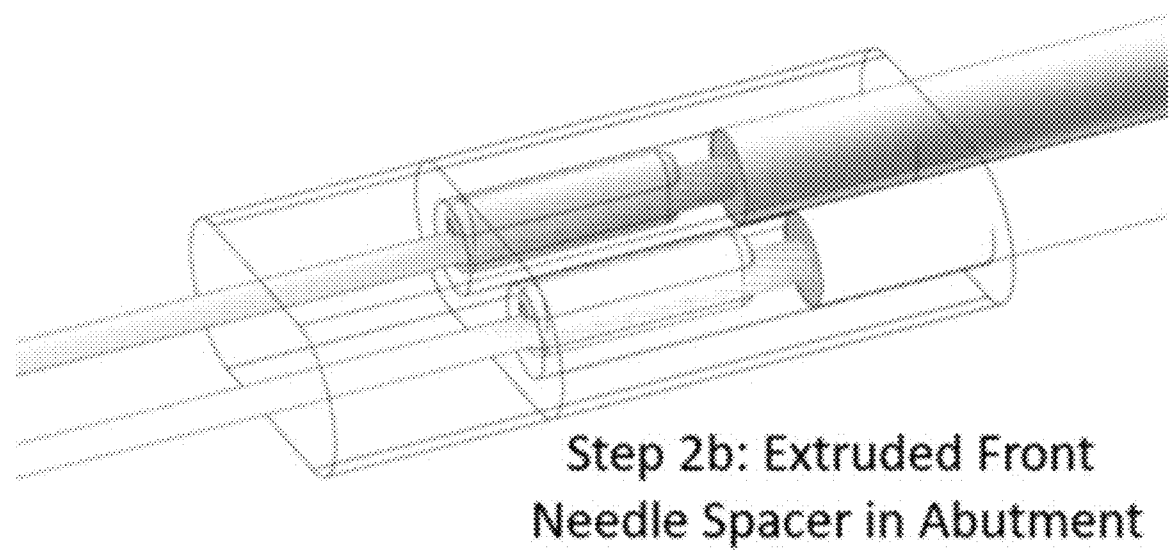
Figure 17D:
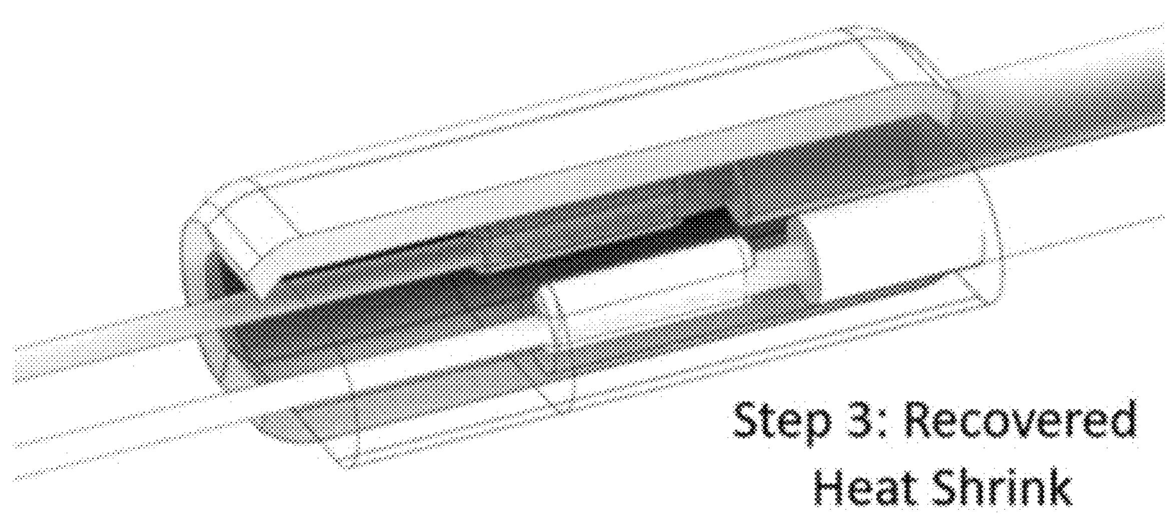

According to some examples, FIGS. 17A, 17B, 17C and 17D show steps of a method of manufacturing a neurodiagnostic needle electrode pair utilizing a needle spacer 700 in abutment with a leadwire spacer 300. FIG. 17A shows a first step which may include soldering together needle electrodes and leadwires to form a neurodiagnostic needle electrode pair subassembly. A second step (Step 2A) may include placing the leadwire spacer 300 over the subassembly, as shown in FIG. 17B. FIG. 17C shows the second step may also include (as Step 2B) placing the needle spacer 700 in abutment to the leadwire spacer 300 in the assembly. A third step may include placing an unrecovered heat shrink tube over the extruded parts and recovering the heat shrink tube to form a hub, as shown in a cutaway view of FIG. 17D.

Figure 18:
FIG. 18 is a flowchart illustrating various steps in a method of forming a neurodiagnostic needle electrode pair assembly shown in FIGS. 13A and 13B, according to some example implementations.
Figure 18:
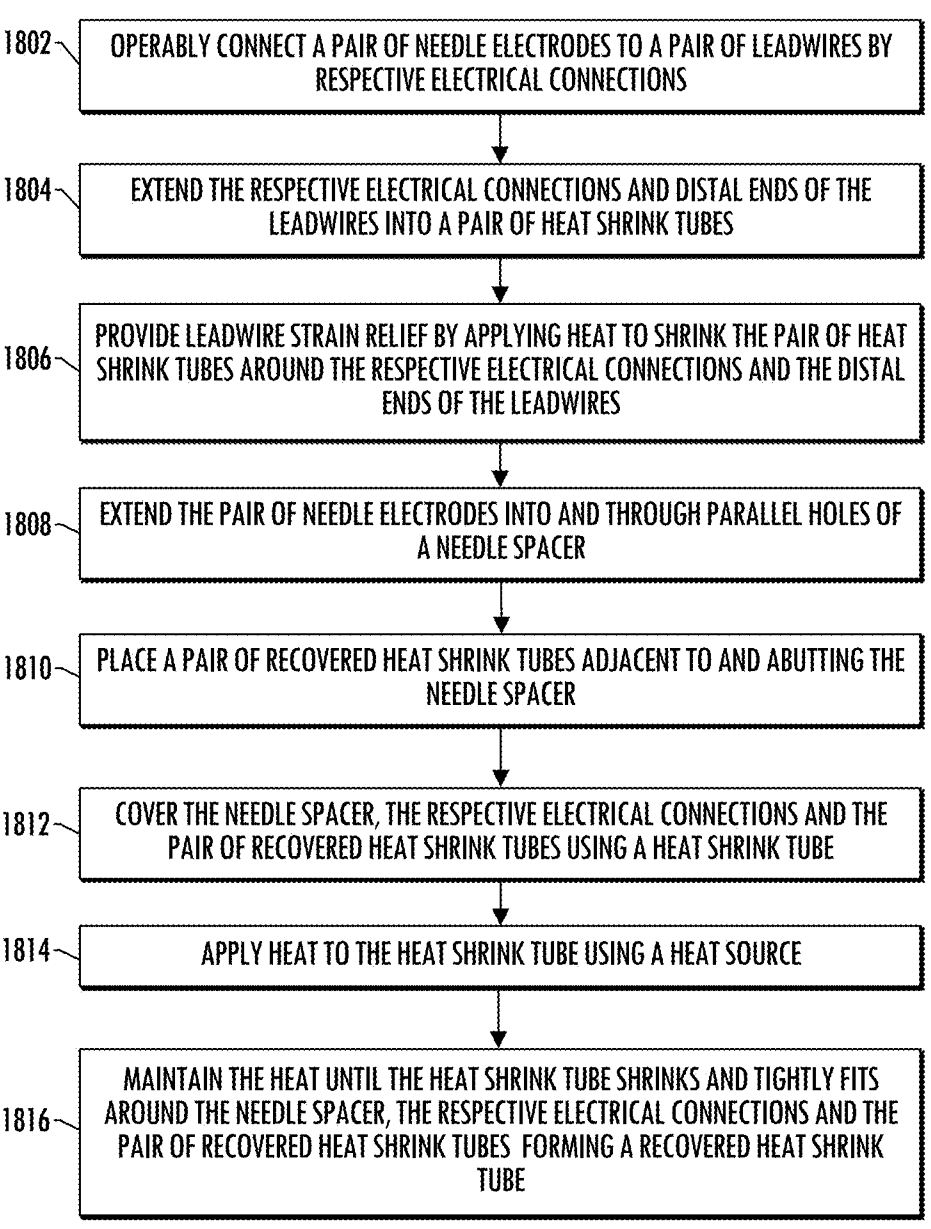

FIG. 18 illustrates a method 1800 of manufacturing a neurodiagnostic needle electrode pair assembly 1300 utilizing a needle spacer 700 in abutment with a pair of heat shrink tubes 400, according to some example implementations. As shown at block 1802, the method may include operably connecting a pair of needle electrodes to a pair of leadwires by respective electrical connections. The method may include extending the respective electrical connections and distal ends of the leadwires into a pair of heat shrink tubes 400, as shown at block 1804. The method may include providing leadwire strain relief by applying heat to shrink the pair of heat shrink tubes 400 around the respective electrical connections and the distal ends of the leadwires, as shown at block 1806. The method may include extending the pair of needle electrodes into and through parallel holes of a needle spacer 700, as shown at block 1808.

The method 1800 may include placing a pair of recovered heat shrink tubes 400 adjacent to and abutting the needle spacer 700, as shown at block 1810. The method may include covering the needle spacer 700, the respective electrical connections and the pair of recovered heat shrink tubes using a heat shrink tube 1002, as shown at block 1812. The method may include applying heat to the heat shrink tube 1002 using a heat source, as shown at block 1814. The method may include maintaining the heat until the heat shrink tube 1002 shrinks and tightly fits around the needle spacer 700, the respective electrical connections and the pair of recovered heat shrink tubes forming a recovered heat shrink tube 1102, as shown at block 1816.

Figure 19A:
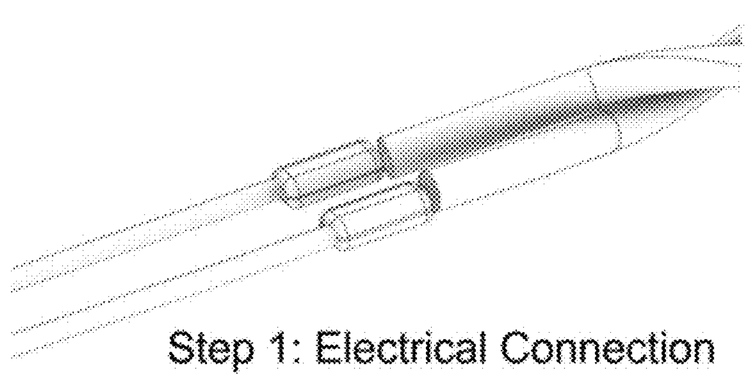
FIGS. 19A, 19B, 19C, 19D and 19E illustrate a process of forming the neurodiagnostic needle electrode pair utilizing a needle spacer and a pair of heat shrink tubes set shown in FIGS. 13A and 13B, according to some example implementations.
Figure 19B:
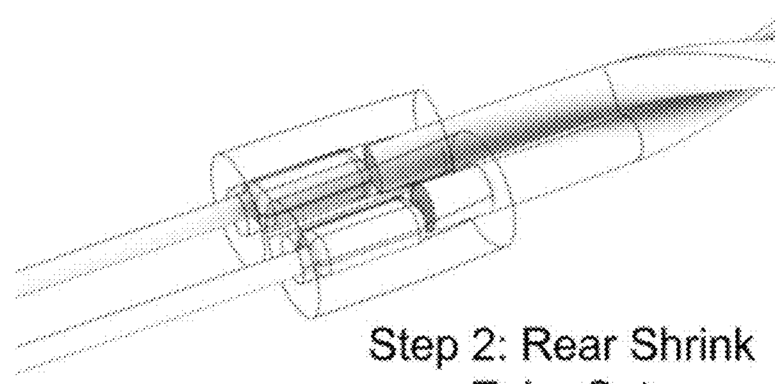
Figure 19C:
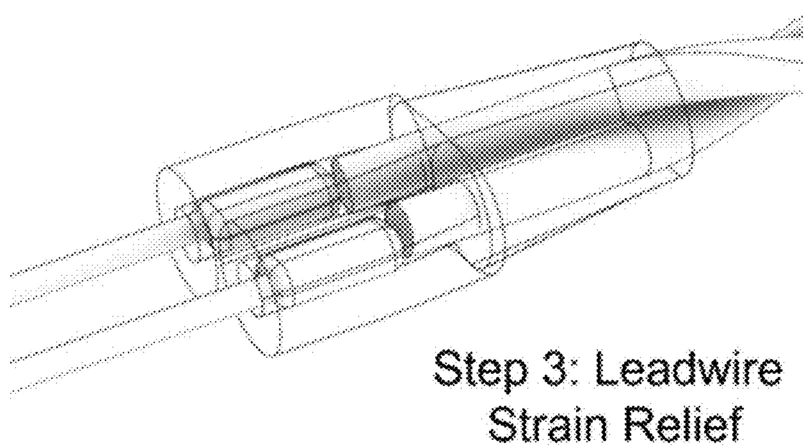
Figure 19D:
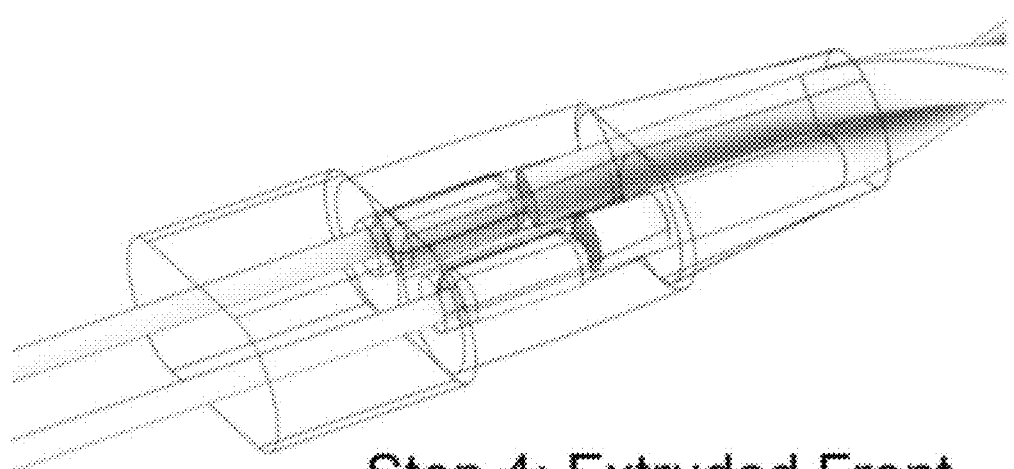
Figure 19E:
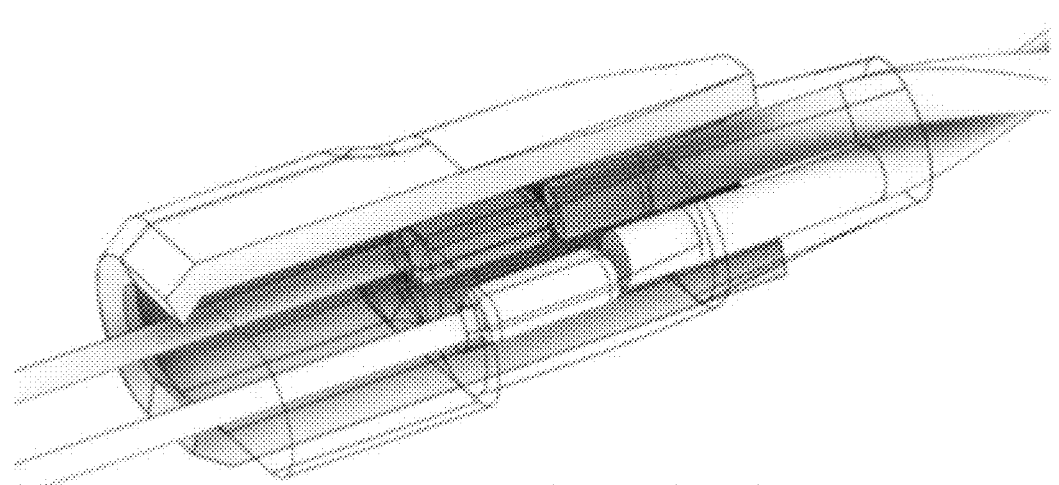

According to other examples, FIGS. 19A, 19B, 19C, 19D and 19E show steps of a method of manufacturing a neurodiagnostic needle electrode pair assembly 1300 utilizing a needle spacer 700 in abutment with a pair of shrink tubes 400. FIG. 19A shows a first step which may include soldering together needle electrodes and leadwires to form a neurodiagnostic needle electrode pair subassembly. A second step (Step 2) may include placing a pair of heat shrink tubes 400 over the subassembly, as shown in FIG. 19B. A third step (Step 3) may include placing the pair of heat shrink tubes 400 over the paired leadwire to act as a strain relief, as shown in FIG. 19C. FIG. 19D shows the fourth step which may include (as Step 4) placing the needle spacer 700 in abutment to the pair of the heat shrink tubes 400 in the assembly. A fifth step may include (as Step 5) placing an unrecovered heat shrink tube 1002 over the assembly and recovering the heat shrink tube 1002 to form a hub, as shown in the cutaway view of FIG. 19E.

Figures 20, 21, 22:
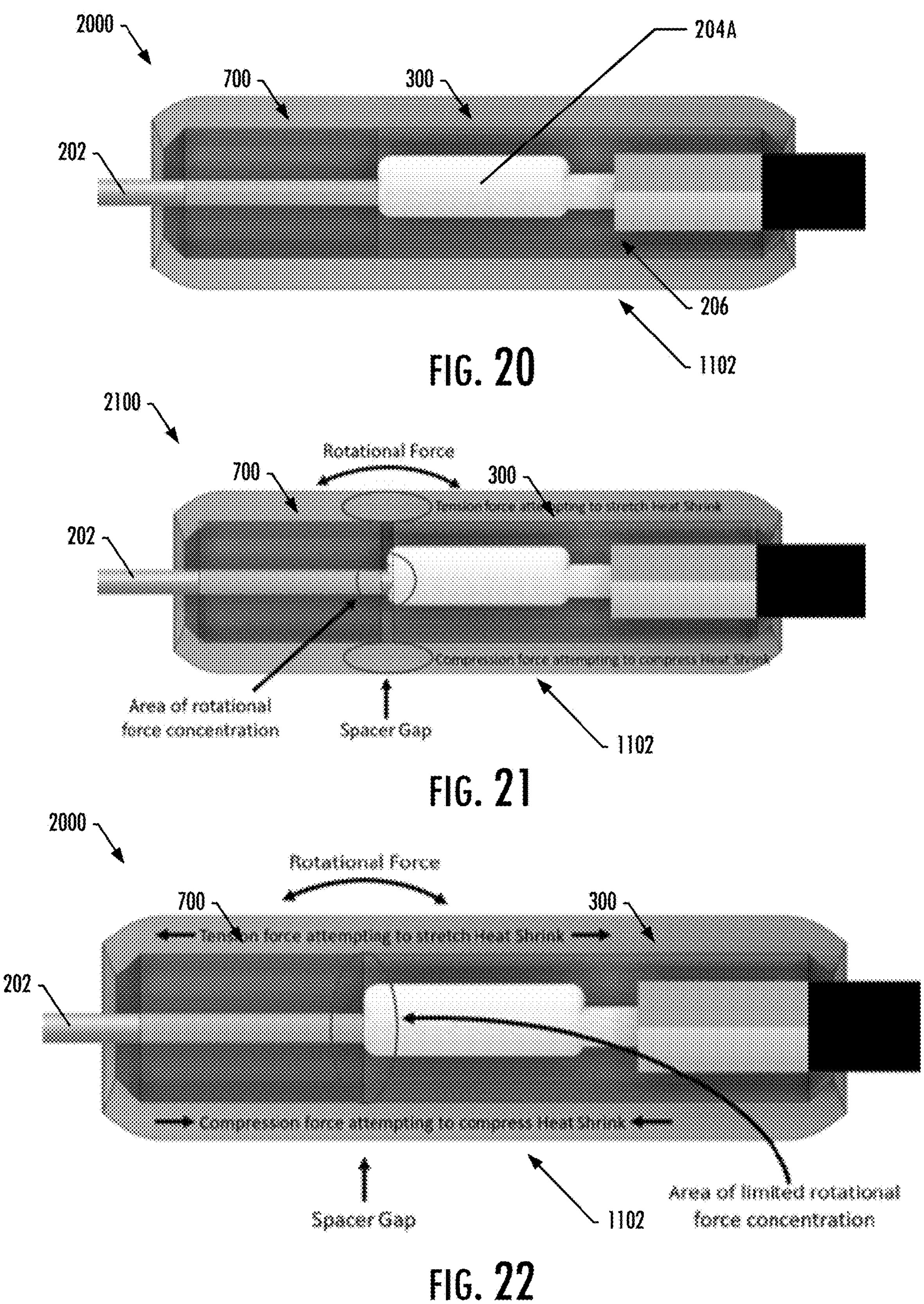
FIG. 20 illustrates a side-view of a cross-section of the neurodiagnostic needle electrode pair utilizing a needle spacer and a leadwire spacer, according to some example implementations.
FIGS. 21 and 22 illustrate alternative side-views of a cross-section of the neurodiagnostic needle electrode pair utilizing a needle spacer and a leadwire spacer, according to some example implementations.

FIG. 20 shows an example of a side view 2000 of a cross-section of an implementation of the neurodiagnostic needle electrode pair utilizing a needle spacer 700 and a leadwire spacer 300. FIGS. 21 and 22 show a side-view 2100 of an alternate implementation of the neurodiagnostic needle electrode pair, as compared to the side view 2000 shown in FIG. 20. The side views of the cross-section illustrate physical features and assembly design characteristics of the finished hub and highlight its structural integrity.

Figures 23, 24, 25:
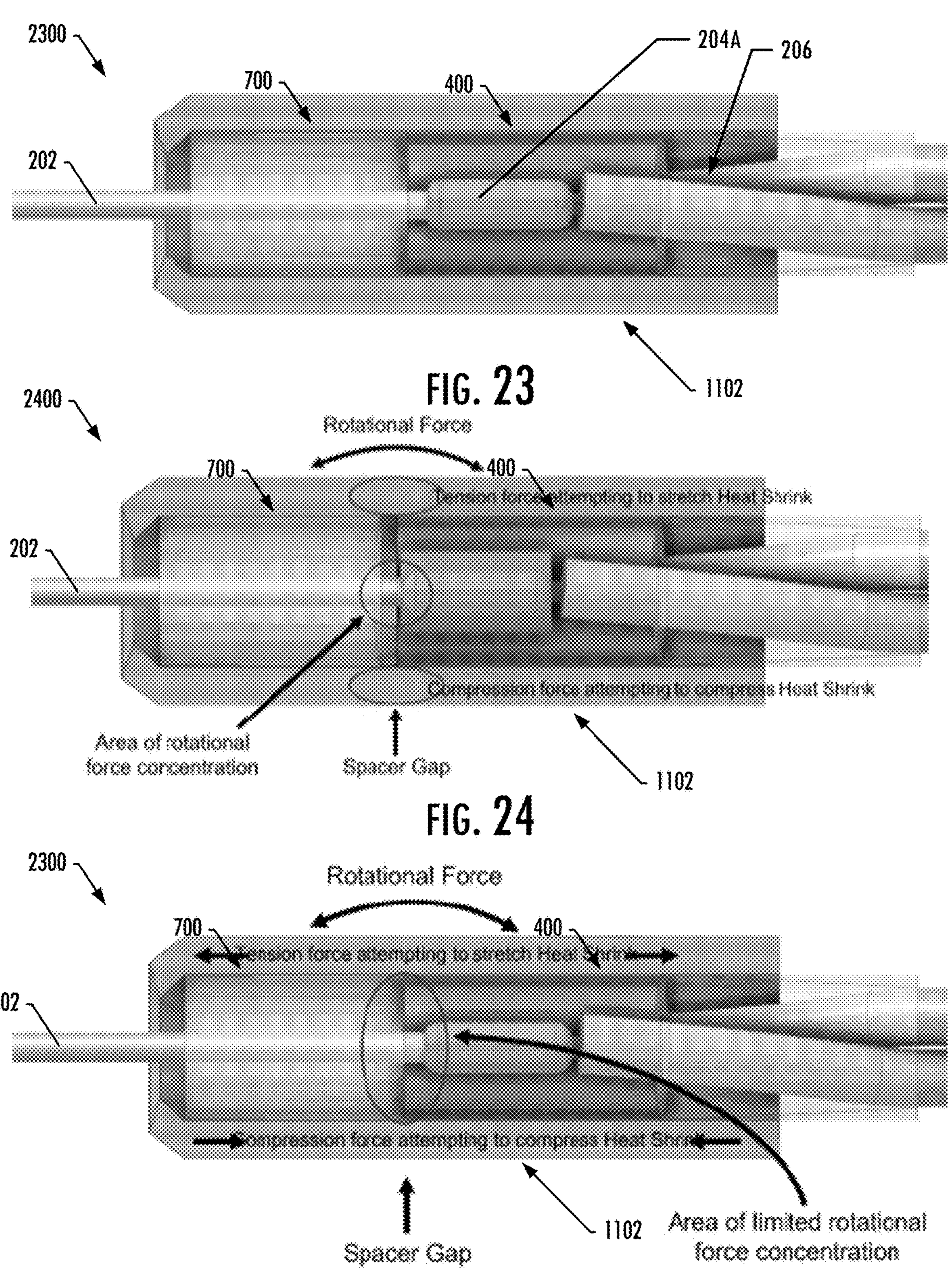
FIG. 23 illustrates a side-view of a cross-section of the neurodiagnostic needle electrode pair utilizing a needle spacer and a pair of heat shrink tubes, according to some example implementations.
FIGS. 24 and 25 illustrate a side-view of a cross-section of the neurodiagnostic needle electrode pair utilizing a needle spacer and a pair of heat shrink tubes, according to some example implementations.

FIG. 23 shows an example of a side view 2300 of a cross-section of an implementation of the neurodiagnostic needle electrode pair utilizing a needle spacer 700 and a pair of heat shrink tubes 400. FIGS. 24 and 25 show a side-view 2400 of an alternate implementation of the neurodiagnostic needle electrode pair, as compared to the side view 2300 shown in FIG. 23. The side views of the cross-section illustrate physical features and assembly design characteristics of the finished hub and highlight its structural integrity.

As mentioned earlier, one or more structural characteristics of the neurodiagnostic needle electrode pair may be to create fluid resistance and physical needle separation with inter-needle rigidity. The needle spacer may be manufactured with these characteristics in mind. Having the durometer of the needle spacer of sufficient flexibility to slip onto the needles while ever-so-slightly expanding ensures a fluid-tight fit onto the needles. In addition, the solid fit nature of the needle spacer facilitates a parallel needle orientation hold/grip to maintain needle inter-distance rigidity. The needle spacer thereby creates a consistent parallel needle grip.

Further hub rigidity may be obtained by securing the needle spacer 700 in abutment with the leadwire spacer 300. FIG. 21 illustrates the side-view 2100 of a cross-section of the neurodiagnostic needle electrode pair utilizing the needle spacer 700 and the leadwire spacer 300. In this example there is a spacer gap between the extruded plastic parts. The spacer gap displays a weak point that may be susceptible to rotational forces, thus allowing a concentration of strain centering around the highlighted "area of rotational force concentration."

By placing the needle spacer and the leadwire spacer in abutment, as shown in the example of FIG. 22, the following benefits may be obtained: the "weak" area of rotational force concentration may be substantially limited by being distributed; the areas of force concentration in tension and compression in the heat shrink may be greatly spread out and thus less-concentrated; and the recovered heat shrink forms what amounts to an exoskeleton, creating compression or tension forces to resist bending of the hub. The resultant hub may be adequately stiff and fluid-tight to meet structural requirements in an economical fashion.

When considering the needle spacer with the rear shrink tube set, further hub rigidity may be obtained by securing the needle spacer in abutment with the rear shrink tube set. FIG. 24 illustrates a side-view 2400 of a cross-section of the neurodiagnostic needle electrode pair utilizing a needle spacer 700 and a pair of heat shrink tubes 400. In this example there is a spacer gap between the needle spacer and the rear shrink tube set.

By placing the needle spacer and the rear shrink tube set in abutment, as shown in the example of FIG. 25, the following benefits may be obtained: the "weak" area of rotational force concentration may be substantially limited by being distributed; the areas of force concentration in tension and compression in the heat shrink may be greatly spread out and thus less-concentrated; and the recovered heat shrink forms what amounts to an exoskeleton, creating compression or tension forces to resist bending of the hub. The resultant hub may be adequately stiff and fluid-tight to meet structural requirements in an economical fashion.

Figure 26A:
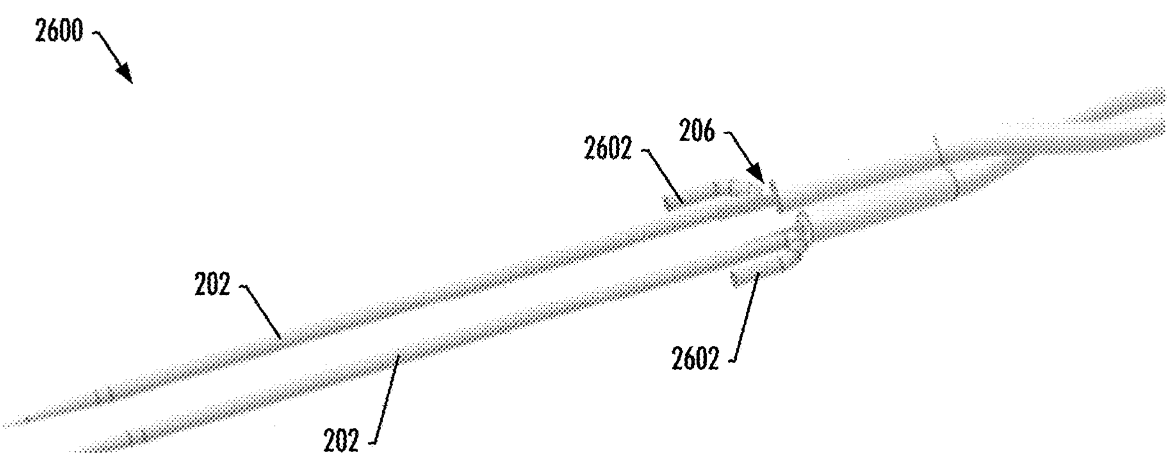
FIGS. 26A and 26B illustrate neurodiagnostic needle electrode pair subassemblies, according to some example implementations.
Figure 26B:
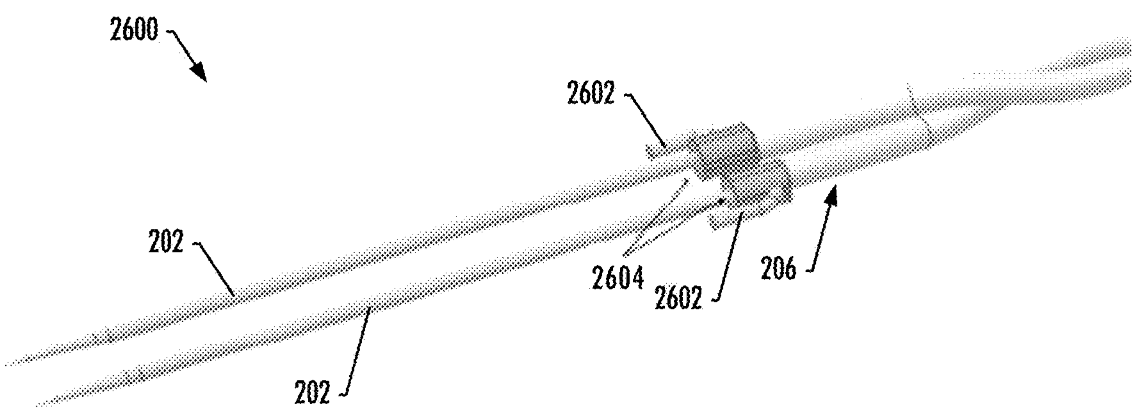

The example of FIGS. 26A and 26B illustrate a subassembly 2600 in which a proximal end of each needle 202 in the pair of needle electrodes has a bend that forms a bent needle end 2602 near which the needle electrode 202 is mechanically crimped to the leadwire 206. In some examples, soldering or other means of performing electrical and mechanical connection of the needle electrode 202 to the leadwire 206 may be utilized instead of mechanical crimp 2604. In some examples, the mechanical crimp 2604 may have a non-circular cross-section (for instance, an oval) that may enhance resistance of the needle electrodes to spin when the needle electrodes are further bent into a bent-needle configuration.

Figure 27A:
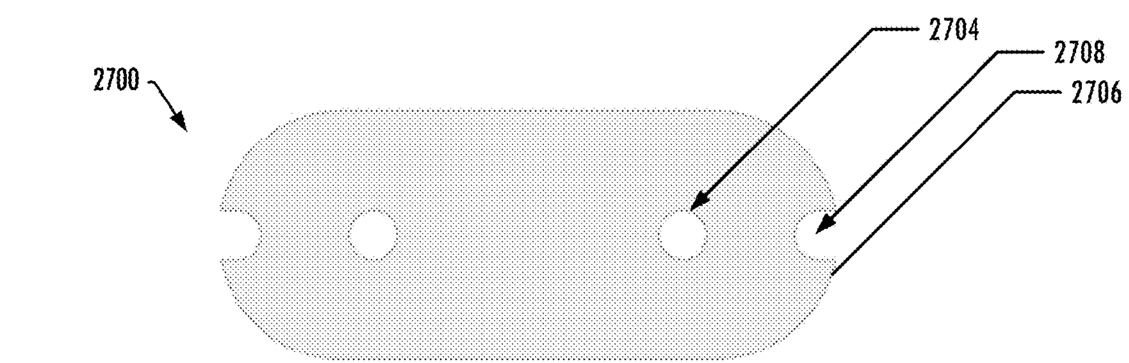
FIGS. 27A, 27B and 27C illustrate an extruded needle spacer with side slots, according to some example implementations.
Figure 27B:
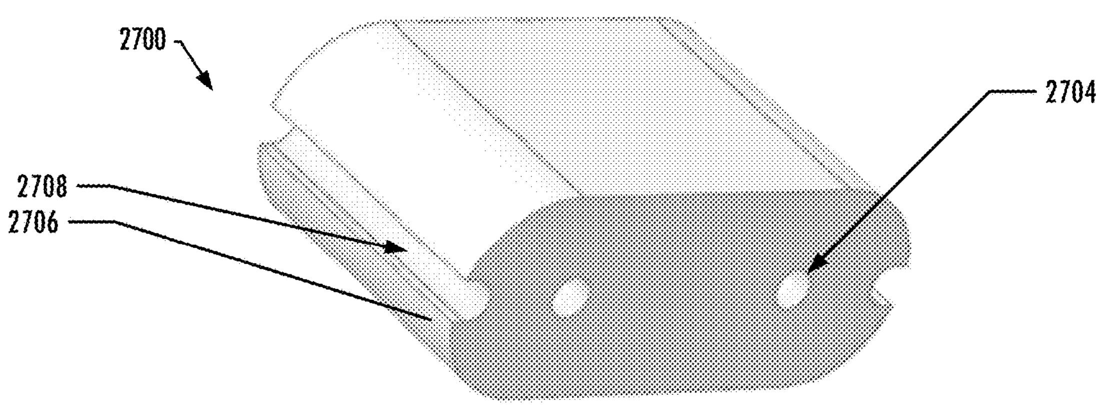
Figure 27C:
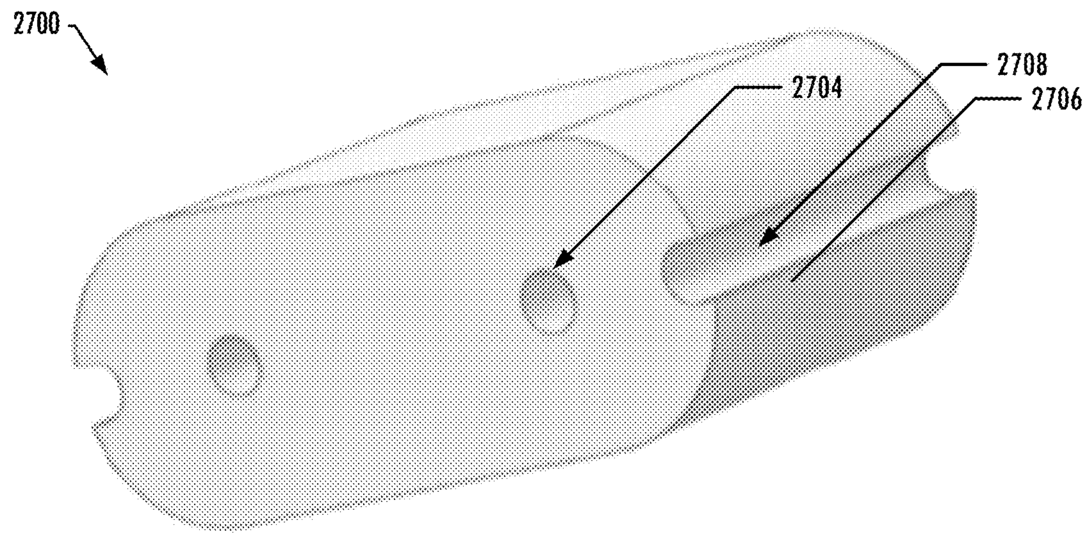

In some examples, an extruded high durometer (yet still somewhat flexible) plastic part is added to the subassembly, as shown in FIGS. 27A-27C. FIG. 27A shows a front view of a needle spacer 2700 with slots 2708 on its outer surface 2706 along the length of the needle spacer 2700, while FIGS. 27B and 27C show perspective views of the needle spacer 2700 with the slots 2708. The size of each of two parallel holes 2704 may be configured to allow the needle spacer 2700 with slots 2708 to slide onto the two needle electrodes 202 to create a fluid barrier. The hole size may also create a desired inter-needle parallel distancing, thereby facilitating a secure fitting that holds the needles in a secure position.

FIG. 28A shows a subassembly 2800 in which the needle spacer 2700 with slots 2708 placed adjacent to and abutting the mechanically crimped needles in such a way that the bent needle ends 2602 slide into the slots 2708 of the needle spacer 2700. FIGS. 28B and 28C shows alternative views of FIG. 28A.

Figure 28D:
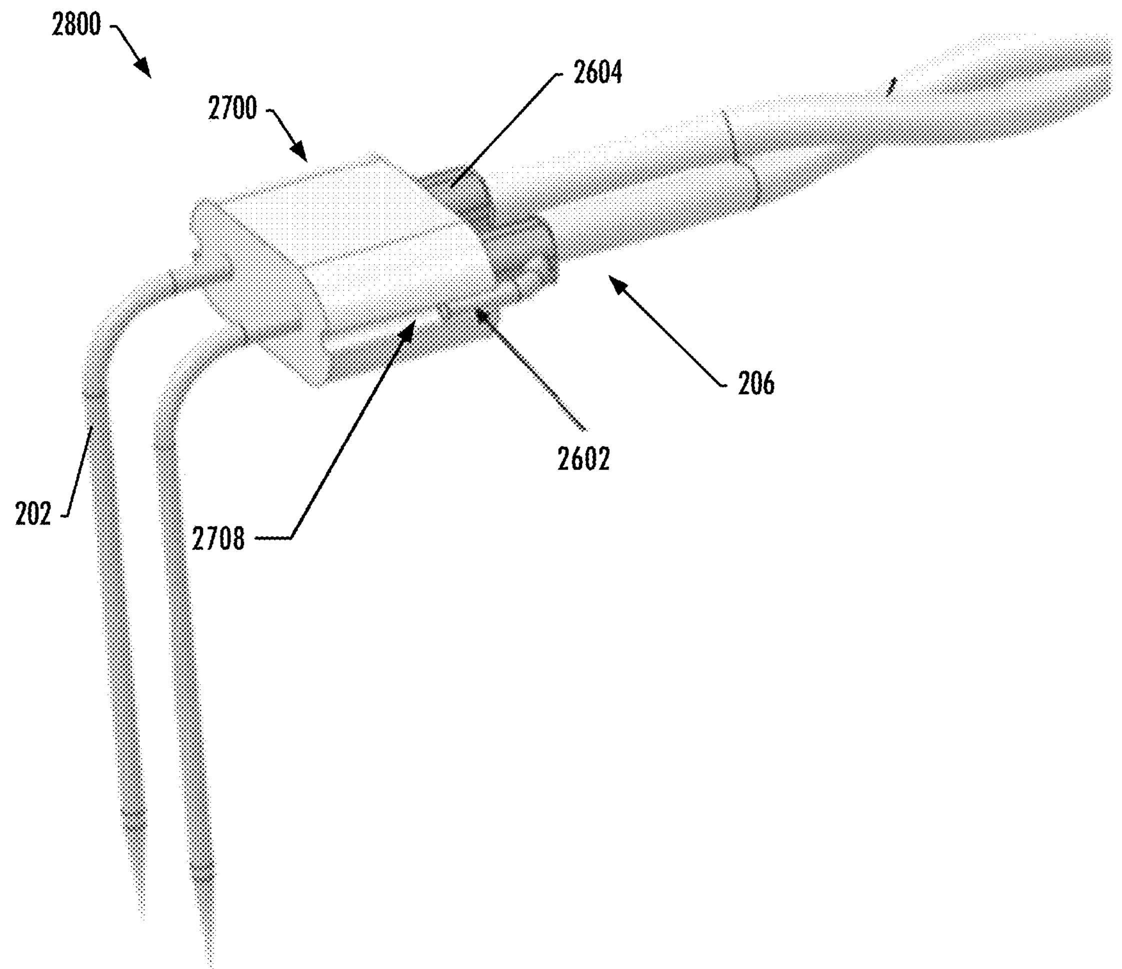

In some examples, the needle electrodes 202 used in the neurodiagnostic needle electrode pair as shown in FIGS. 28A-28C may be further bent in a manner the same as or similar to that shown and described earlier with respect to FIGS. 14 and 15. FIG. 28D shows the same example but with neurodiagnostic needle electrode pair bent at a 90-degree angle.

Figure 29A:
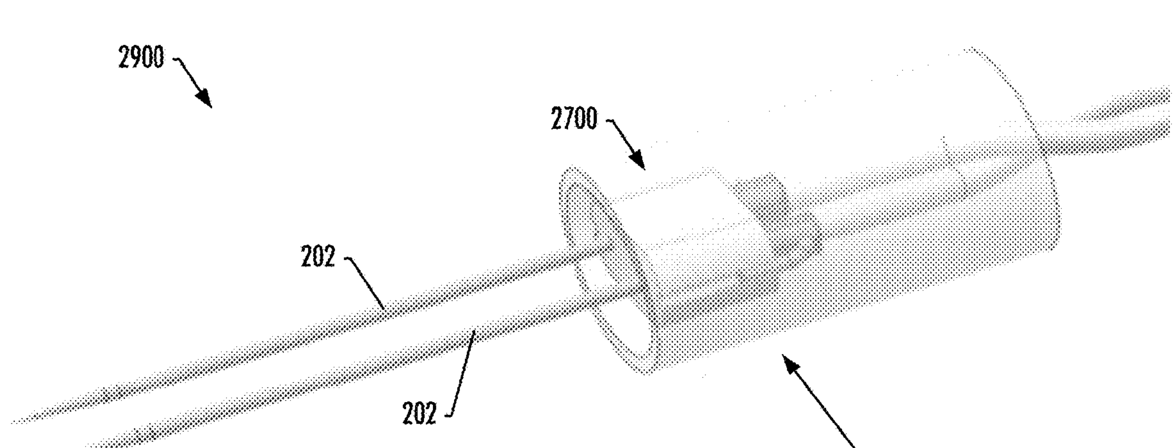
FIGS. 29A and 29B illustrate the placement of thermoplastic shrinkable tubing over the extruded needle spacer with side slots in abutment with mechanically crimped needles, according to some example implementations.
Figure 29B:
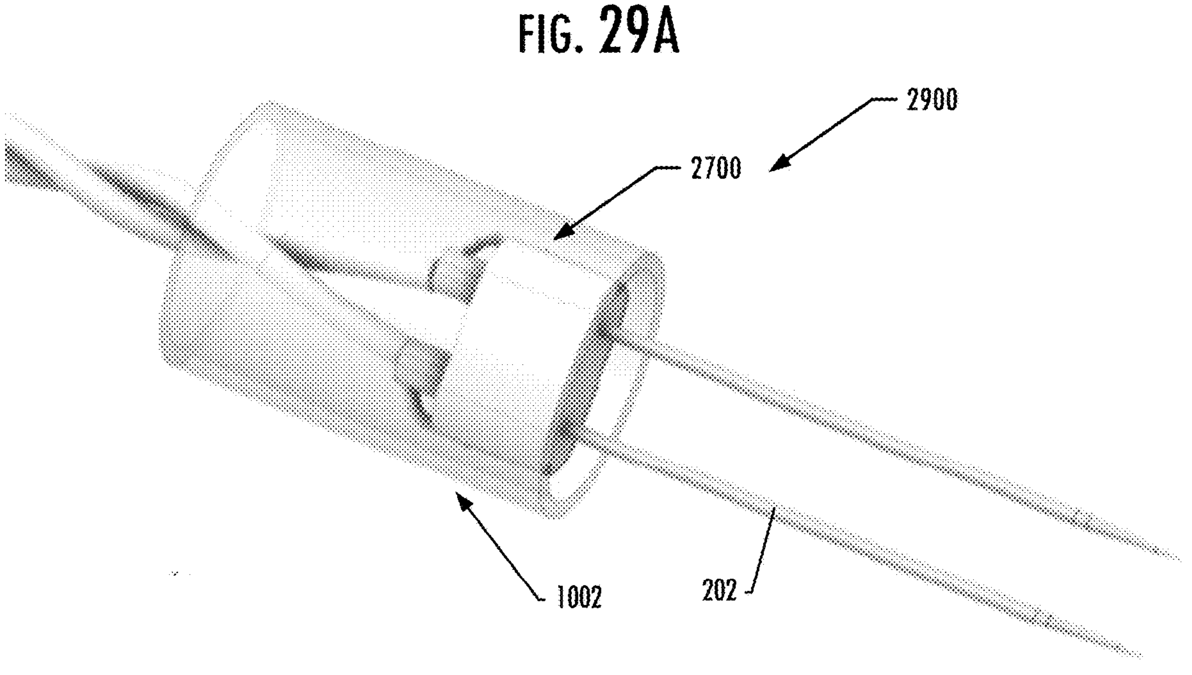

In some examples, a thermoplastic shrinkable tubing (heat shrink tube 1002) is placed (unrecovered) over the needle spacer 2700 with the slots 2708 in abutment with the mechanically crimped needles, as transparently shown in a subassembly 2900 of FIGS. 29A and 29B. In some example implementations, an adhesive-lined heat shrink may be used to flood the underlying components with glue that will harden, further enhancing the resistance of the needle electrodes to spin when in bent configuration, as well as enhancing fluid resistance of the assembly. In these examples, when the heat shrink tube 1002 is recovered (i.e., shrank), the combination of the needle spacer 2700 with slots 2708 in abutment with the mechanically crimped needles and the recovered heat shrink tube 1102 form what amounts to a solid unit (i.e., a hub) with limited flexibility and functionally equivalent in form factor to an injection molded hub. FIGS. 30A and 30B show angular views of a neurodiagnostic needle electrode pair assembly 3000 in which the recovered heat shrink 1102 is over the needle spacer 2700 with side slots 2708 in abutment with the mechanically crimped needles forming a hub. The resultant hub thereby appears as a solid unit in its construction.

FIG. 31 illustrates a method 3100 of manufacturing a neurodiagnostic needle electrode pair assembly 3000 utilizing a needle spacer 2700 with slots 2708 in abutment with the mechanically crimped needles, according to some example implementations. As shown at block 3102, the method may include operably connecting the bent needle ends 2602 of a pair of needle electrodes to a pair of leadwires by respective electrical connections. The method may include sliding a needle spacer 2700 having the slots 2708 along a length of the pair of needle electrodes, as shown at block 3104. The method may include extending the bent needle ends 2602 of the needle electrodes 202 into the slots 2708 of the needle spacer 2700, as shown at block 3106. The method may include covering the needle spacer 2700 and the respective electrical connections using a heat shrink tube 1002, as shown at block 3108.

The method 3100 may include applying heat to the heat shrink tube 1002 using a heat source, as shown at block 3110. The method may include maintaining the heat until the heat shrink tube 1002 shrinks and tightly fits around the needle spacer 2700 and the respective electrical connections forming a recovered heat shrink tube 1102, as shown at block 3112.

Figure 32A:
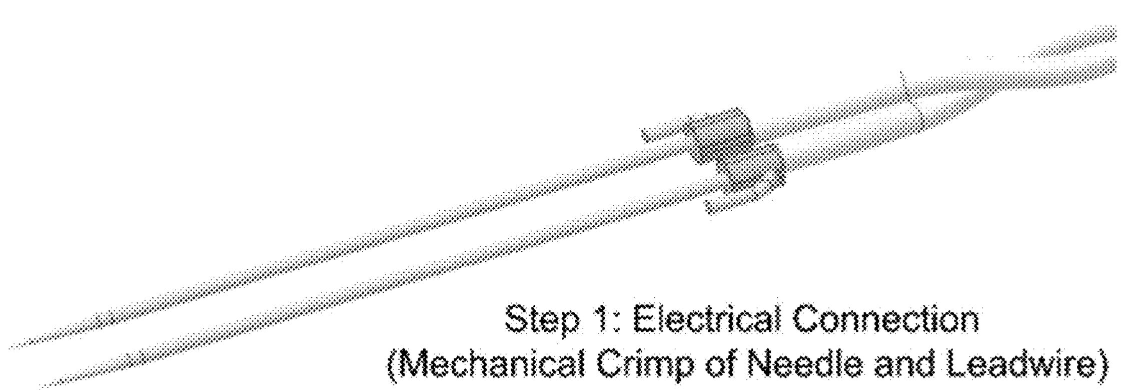
Figure 32B:
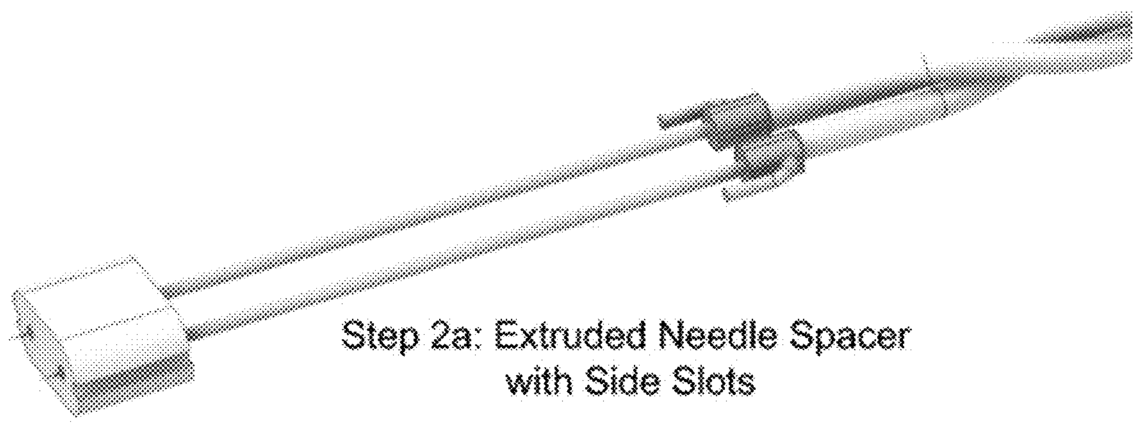
Figure 32C:
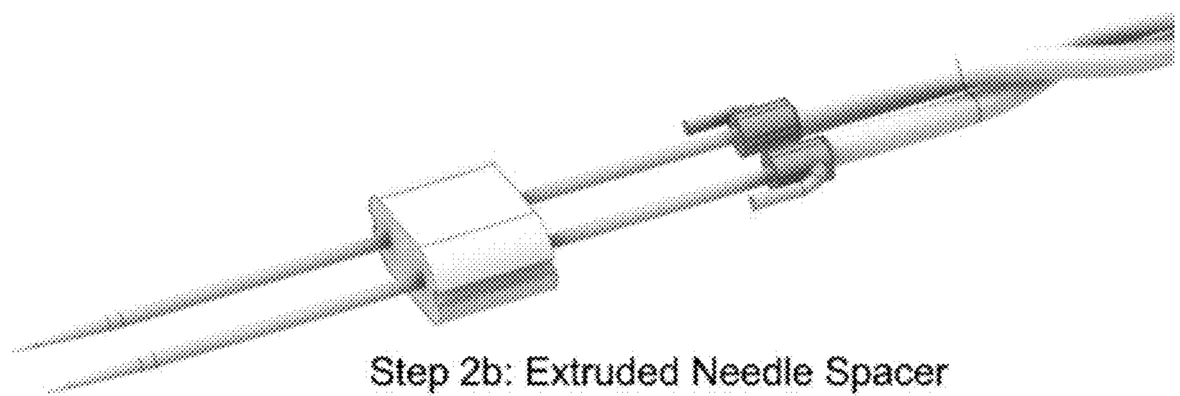
Figure 32D:
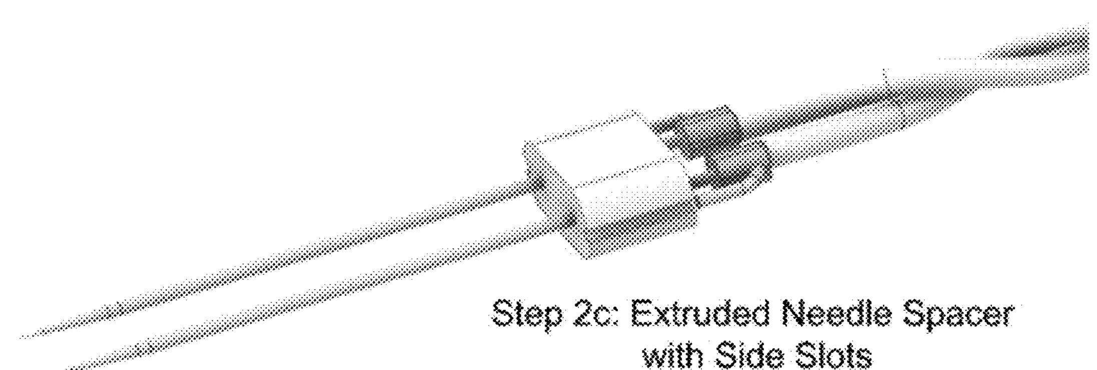
Figure 32E:
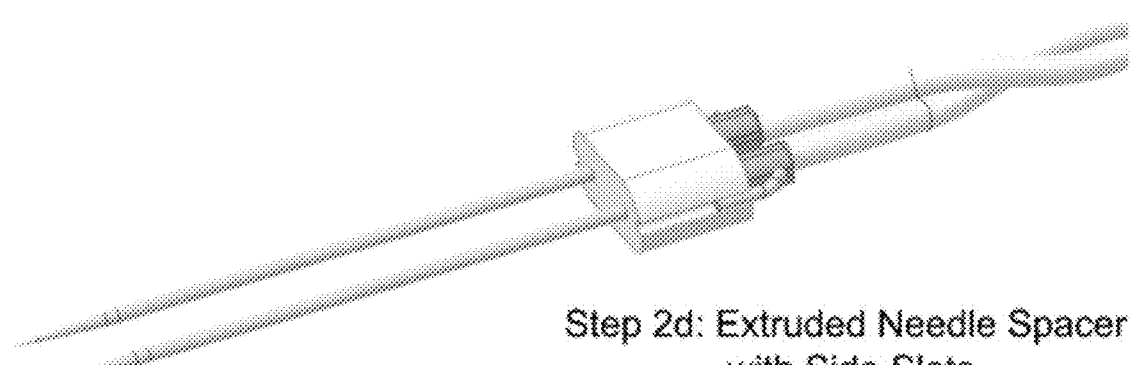
Figure 32F:
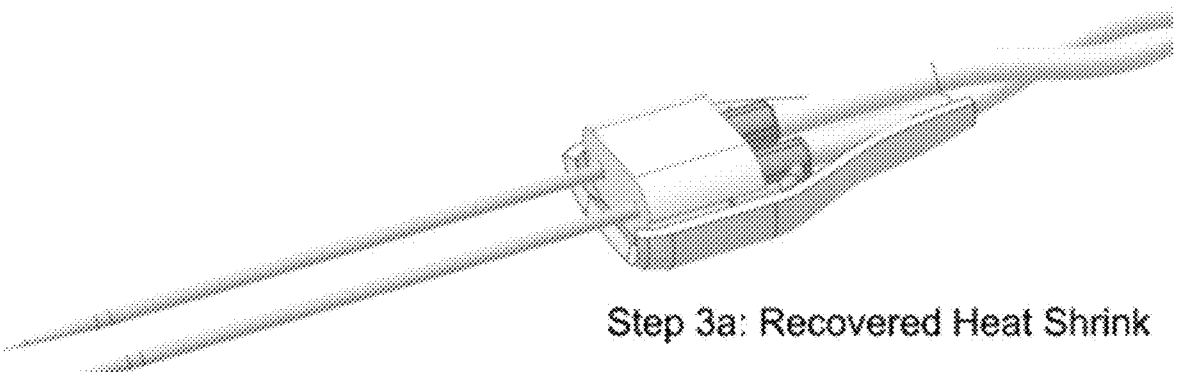
Figure 32G:
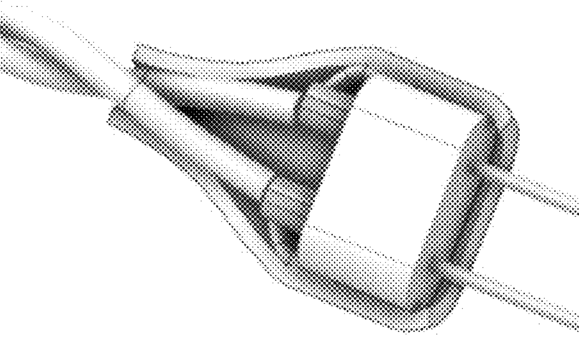

According to some examples, FIGS. 32A, 32B, 32C, 32D, 32E, 32F and 32G show steps of a method of manufacturing a neurodiagnostic needle electrode pair assembly 3000 utilizing a needle spacer 2700 with slots 2708 in abutment with the mechanically crimped needles. FIG. 32A shows a first step which may include mechanically crimping together needle electrodes and leadwires to form a neurodiagnostic needle electrode pair subassembly. A second step (step 2A) may include placing a needle spacer 2700 with slots 2708 over the subassembly, as shown in FIGS. 32B-32E. A third step may include placing an unrecovered heat shrink tube over the extruded parts and recovering the heat shrink tube to form a hub, as shown in a cutaway view of FIGS. 32F and 32G.

In various configurations including in particular a bent-needle configuration such as that shown in FIG. 28D, a force applied to distal end of a needle electrode in the needle pair may produce a torque on the needle electrode within the needle spacer. This torque may in turn promote spin of the needle axially within the extruded needle spacer. A fluid-tight fit of the extruded needle spacer on the needle may resist this spin, and this resistance to spin may be further enhanced by the bent needle end of the needle, in one of the side slots of the extruded needle spacer.

As explained above and reiterated below, the present disclosure includes, without limitation, the following example implementations.

Clause 1. A neurodiagnostic needle electrode pair assembly comprising: a pair of needle electrodes connected to a pair of leadwires by respective electrical connections between proximal ends of the needle electrodes and distal ends of the leadwires; a needle spacer including parallel holes in a spaced apart relationship, the needle electrodes extending into and through the parallel holes that define a spacing between the needle electrodes; and a recovered heat shrink tube covering the needle spacer, the respective electrical connections and the distal ends of the leadwires.

Clause 2. The neurodiagnostic needle electrode pair assembly of clause 1, wherein the needle spacer is an extrusion having a fixed cross-sectional profile.

Clause 3. The neurodiagnostic needle electrode pair assembly of clause 1 or clause 2, further comprising a leadwire spacer adjacent to and abutting the needle spacer, and that includes second parallel holes in a spaced apart relationship, the respective electrical connections and the distal ends of the leadwires extending into the second holes that define a spacing between the leadwires, and wherein the recovered heat shrink tube covers the needle spacer, and the leadwire spacer including the second parallel holes into which the respective electrical connections and the distal ends of the leadwires extend.

Clause 4. The neurodiagnostic needle electrode pair assembly of clause 3, wherein the respective electrical connections include mechanical crimps, and the mechanical crimps and the second parallel holes of the leadwire spacer have matching, non-circular cross sections.

Clause 5. The neurodiagnostic needle electrode pair assembly of clause 3 or clause 4, wherein the leadwire spacer includes a pair of adjacent, recovered heat shrink tubes that include respective ones of the second parallel holes.

Clause 6. The neurodiagnostic needle electrode pair assembly of any of clauses 3 to 5, wherein the leadwire spacer is an extrusion having a fixed cross-sectional profile.

Clause 7. The neurodiagnostic needle electrode pair assembly of any of clauses 3 to 6, wherein the needle spacer and the leadwire spacer are extrusions having a common, fixed cross-sectional profile.

Clause 8. The neurodiagnostic needle electrode pair assembly of any of clauses 3 to 7, wherein the recovered heat shrink tube includes an inner adhesive lining that adheres the recovered heat shrink tube to the needle spacer and the leadwire spacer.

Clause 9. The neurodiagnostic needle electrode pair assembly of any of clauses 1 to 8, wherein the parallel holes of the needle spacer have a non-circular cross section.

Clause 10. The neurodiagnostic needle electrode pair assembly of any of clauses 1 to 9, wherein the needle electrodes are bent near the proximal ends to form bent needle ends near the respective electrical connections, and wherein the needle spacer further includes slots into which the bent needle ends extend.

Clause 11. The neurodiagnostic needle electrode pair assembly of any of clauses 1 to 10, wherein the recovered heat shrink tube includes an inner adhesive lining that adheres the recovered heat shrink tube to the needle spacer, the respective electrical connections and the distal ends of the leadwires.

Clause 12. A method of manufacturing a neurodiagnostic needle electrode pair assembly, the method comprising: connecting a pair of needle electrodes to a pair of leadwires by forming respective electrical connections between proximal ends of the needle electrodes and distal ends of the leadwires; extending the needle electrodes into and through parallel holes of a needle spacer, the parallel holes defining a spacing between the needle electrodes; positioning a heat shrink tube over the needle spacer, the respective electrical connections and the distal ends of the leadwires; and applying heat to recover the heat shrink tube covering the needle spacer, the respective electrical connections, and the distal ends of the leadwires.

Clause 13. The method of clause 12, wherein the needle spacer is an extrusion having a fixed cross-sectional profile.

Clause 14. The method of clause 12 or clause 13, wherein before the pair of needle electrodes are extended into and through the parallel holes of the needle spacer, the method further comprises: extending the needle electrodes into and through second parallel holes of a leadwire spacer, and the respective electrical connections and the distal ends of the leadwires into the second holes that define a spacing between the leadwires.

Clause 15. The method of clause 14, wherein the pair of needle electrodes are extended into and through the parallel holes of the needle spacer to position the needle spacer adjacent to and abutting the leadwire spacer, and wherein the heat shrink tube is positioned over the needle spacer and the leadwire spacer, and the heat is applied to recover the heat shrink tube covering the needle spacer, and the leadwire spacer including the second parallel holes into which the respective electrical connections and the distal ends of the leadwires extend.

Clause 16. The method of clause 14 or clause 15, wherein the respective electrical connections include mechanical crimps, and the mechanical crimps and the second parallel holes of the leadwire spacer have matching, non-circular cross sections.

Clause 17. The method of any of clauses 14 to 16, wherein the leadwire spacer includes a pair of adjacent, recovered heat shrink tubes that include respective ones of the second parallel holes.

Clause 18. The method of any of clauses 14 to 17, wherein the needle spacer and the leadwire spacer are extrusions having a common, fixed cross-sectional profile.

Clause 19. The method of any of clauses 12 to 18, wherein the needle electrodes are bent near the proximal ends to form bent needle ends near the respective electrical connections, and the needle spacer further includes slots, and wherein extending the needle electrodes into and through parallel holes of the needle spacer includes extending the bent needle ends into the slots of the needle spacer.

Clause 20. The method of clause 19, wherein the heat shrink tube is positioned over the needle spacer and the leadwire spacer, and includes an inner adhesive lining that adheres the recovered heat shrink tube to the needle spacer and the leadwire spacer.

Many modifications and other implementations of the disclosure set forth herein will come to mind to one skilled in the art to which the disclosure pertains having the benefit of the teachings presented in the foregoing description and the associated figures. Therefore, it is to be understood that the disclosure is not to be limited to the specific implementations disclosed and that modifications and other implementations are intended to be included within the scope of the appended claims. Moreover, although the foregoing description and the associated figures describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A neurodiagnostic needle electrode pair assembly comprising:

a pair of needle electrodes connected to a pair of leadwires by respective electrical connections between proximal ends of the needle electrodes and distal ends of the leadwires;

a needle spacer including parallel holes in a spaced apart relationship, the needle electrodes extending into and through the parallel holes that define a spacing between the needle electrodes;

a recovered heat shrink tube covering the needle spacer, the respective electrical connections and the distal ends of the leadwires and a leadwire spacer adjacent to and abutting the needle spacer, and that includes second parallel holes in a spaced apart relationship, the respective electrical connections and the distal ends of the leadwires extending into the second holes that define a spacing between the leadwires, and wherein the recovered heat shrink tube covers the needle spacer, and the leadwire spacer including the second parallel holes into which the respective electrical connections and the distal ends of the leadwires extend.

2. The neurodiagnostic needle electrode pair assembly of claim 1, wherein the needle spacer is an extrusion having a fixed cross-sectional profile.

3. The neurodiagnostic needle electrode pair assembly of claim 1, wherein the respective electrical connections include mechanical crimps, and the mechanical crimps and the second parallel holes of the leadwire spacer have matching, non-circular cross sections.

4. The neurodiagnostic needle electrode pair assembly of claim 1, wherein the leadwire spacer includes a pair of adjacent, recovered heat shrink tubes that include respective ones of the second parallel holes.

5. The neurodiagnostic needle electrode pair assembly of claim 1, wherein the leadwire spacer is an extrusion having a fixed cross-sectional profile.

6. The neurodiagnostic needle electrode pair assembly of claim 1, wherein the needle spacer and the leadwire spacer are extrusions having a common, fixed cross-sectional profile.

7. The neurodiagnostic needle electrode pair assembly of claim 1, wherein the recovered heat shrink tube includes an inner adhesive lining that adheres the recovered heat shrink tube to the needle spacer and the leadwire spacer.

8. The neurodiagnostic needle electrode pair assembly of claim 1, wherein the parallel holes of the needle spacer have a non-circular cross section.

9. The neurodiagnostic needle electrode pair assembly of claim 1, wherein the needle electrodes are bent near the proximal ends to form bent needle ends near the respective electrical connections, and wherein the needle spacer further includes slots into which the bent needle ends extend.

10. The neurodiagnostic needle electrode pair assembly of claim 1, wherein the recovered heat shrink tube includes an inner adhesive lining that adheres the recovered heat shrink tube to the needle spacer, the respective electrical connections and the distal ends of the leadwires.

11. A method of manufacturing a neurodiagnostic needle electrode pair assembly, the method comprising:

connecting a pair of needle electrodes to a pair of leadwires by forming respective electrical connections between proximal ends of the needle electrodes and distal ends of the leadwires;

extending the needle electrodes into and through parallel holes of a needle spacer, the parallel holes defining a spacing between the needle electrodes;

positioning a heat shrink tube over the needle spacer, the respective electrical connections and the distal ends of the leadwires;

applying heat to recover the heat shrink tube covering the needle spacer, the respective electrical connections, and the distal ends of the leadwires and wherein before the pair of needle electrodes are extended into and through the parallel holes of the needle spacer, the method further comprises: extending the needle electrodes into and through second parallel holes of a leadwire spacer, and the respective electrical connections and the distal ends of the leadwires into the second holes that define a spacing between the leadwires.

12. The method of claim 11, wherein the needle spacer is an extrusion having a fixed cross-sectional profile.

13. The method of claim 11, wherein the pair of needle electrodes are extended into and through the parallel holes of the needle spacer to position the needle spacer adjacent to and abutting the leadwire spacer, and wherein the heat shrink tube is positioned over the needle spacer and the leadwire spacer, and the heat is applied to recover the heat shrink tube covering the needle spacer, and the leadwire spacer including the second parallel holes into which the respective electrical connections and the distal ends of the leadwires extend.

14. The method of claim 11, wherein the respective electrical connections include mechanical crimps, and the mechanical crimps and the second parallel holes of the leadwire spacer have matching, non-circular cross sections.

15. The method of claim 11, wherein the leadwire spacer includes a pair of adjacent, recovered heat shrink tubes that include respective ones of the second parallel holes.

16. The method of claim 11, wherein the needle spacer and the leadwire spacer are extrusions having a common, fixed cross-sectional profile.

17. The method of claim 11, wherein the needle electrodes are bent near the proximal ends to form bent needle ends near the respective electrical connections, and the needle spacer further includes slots, and wherein extending the needle electrodes into and through parallel holes of the needle spacer includes extending the bent needle ends into the slots of the needle spacer.

18. The method of claim 17, wherein the heat shrink tube is positioned over the needle spacer and the leadwire spacer, and includes an inner adhesive lining that adheres the recovered heat shrink tube to the needle spacer and the leadwire spacer.

* * * * *